United States Patent [19]
Takeda

[11] Patent Number: 5,623,528
[45] Date of Patent: Apr. 22, 1997

[54] METHOD FOR GENERATING 3-DIMENSIONAL IMAGES

[75] Inventor: Shiro Takeda, Kawasaki, Japan

[73] Assignee: Fujitsu Limited, Kawasaki, Japan

[21] Appl. No.: 207,669

[22] Filed: Mar. 9, 1994

[30] Foreign Application Priority Data

Mar. 24, 1993 [JP] Japan ................................ 5-065278

[51] Int. Cl.$^6$ ................................................ G01N 23/00
[52] U.S. Cl. ................................ 378/2; 378/22; 250/582
[58] Field of Search ................................ 378/2, 21–25, 378/41, 43, 171; 250/582, 583

[56] References Cited

U.S. PATENT DOCUMENTS

| | | | |
|---|---|---|---|
| 4,416,018 | 11/1983 | Curth et al. | 378/2 |
| 4,439,866 | 3/1984 | Kato et al. | 250/583 |

FOREIGN PATENT DOCUMENTS

| | | |
|---|---|---|
| 3344494A1 | 6/1985 | Germany . |
| 3841414A1 | 8/1990 | Germany . |
| 4224568A1 | 1/1993 | Germany . |
| 64-2628 | 6/1989 | Japan . |

*Primary Examiner*—Don Wong
*Attorney, Agent, or Firm*—Staas & Halsey

[57] ABSTRACT

An object of the present invention is to provide a novel method for generating 3-dimensional radiation images and, more particularly, a method for generating 3-dimensional radiation images capable of aligning completely registered 3-dimensional positions thereof. At least one 2-dimensional radiation image of a subject carried by a radiant ray which has passed through a subject is obtained by irradiating a radiant ray from a plurality of positions, which differ from one another, toward said subject, 2-dimensional pixel data which denotes pixel values at respective points on said 2-dimensional radiation image is obtained by repeatedly scanning an image in a main scanning direction which intersects a sub-scanning direction while sequentially moving in said specified sub-scanning direction on this 2-dimensional radiation image, and 3-dimensional pixel data which denotes the pixel values corresponding to 3-dimensional points inside said subject are obtained based on the 2-dimensional pixel data.

32 Claims, 17 Drawing Sheets

METHOD FOR GENERATING 3-DIMENSIONAL IMAGES

BACKGROUND OF THE INVENTION

1. Field of the Invention

The present invention relates to a method for generating 3-dimensional radiation images from which 3-dimensional pixel data indicating pixel values of respective 3-dimensional points of a subject are obtained and, more particularly, a method 3-dimensional radiation images for medical treatment, typically 3-dimensional radiation thoracic images.

2. Description of the Related Art

Usually radiation images such as X-ray images have been widely used in medical diagnoses. For example, in the case of X-ray images, an X-ray which has passed through a subject is irradiated onto a phosphor layer (phosphor screen) to convert the X-ray to a visible light, this visible light is irradiated onto a silver halide film to form thereon a latent image, an X-ray image is obtained by developing this film, and the X-ray image thus obtained is used in diagnoses of diseases (hereinafter referred to as the "S/F method".) In this case, there has been a problem that developed X-ray films thus obtained will require a larger space for storage as the number of developed films increases and moreover it is toilsome to select and take out desired X-ray films for comparison in observation of a time-elapsed change of the condition of disease of the same subject (for example, a patient.) Lately, therefore, a system has been used which enables to obtain a reproduced image with high image quality and high diagnostic performance after an X-ray image formed on a silver halide film as described above has been read photoelectrically by the so-called film digitizer to obtain image signals and various image factors such as sharpness, dynamic range and graininess which determine the quality of image and the diagnostic performance for diagnoses of diseases have been improved through image processing of these image signals.

FIG. 1 shows an example configuration of the film digitizer.

An X-ray film on which an X-ray image has been recorded and developed is transferred by transfer rollers 2 along a transfer passage 1. This X-ray film is repeatedly scanned by a laser beam 7 emitted from a laser scanning system 3 in a direction normal to FIG. 1 while being transferred, thereby this X-ray film is raster-scanned in two dimensions. This laser beam 7 is attenuated in accordance with a density of each pixel of the X-ray image recorded on the X-ray film, then transmits the X-ray film and is received by a light receiving element array 5 whereby image signals which bear the X-ray image are generated. When the X-ray image is recorded on a photographic paper, a reflected light of the laser beam 7 irradiated onto this photographic paper is received by the light receiving element 4 and converted into image signals.

On the other hand, a system using an energy accumulating phosphorescent material (accelerated phosphorescence fluorescent material; photo-stimulable phosphor) has begun to be used instead of the above-described system using silver halide films. A system using this accelerated phosphorescence fluorescent material is such that an X-ray image is cumulatively stored on an accelerated phosphorescence fluorescent panel or sheet, which is made up by forming the accelerated phosphorescence fluorescent material in the shape of sheet or panel, by irradiating an X-ray which has passed through a subject onto the accelerated phosphorescence fluorescent panel (or sheet) and this X-ray image is photoelectrically read to obtain image signals and obtains a reproduced image after image-processing these image signals. The basic mode of this system is disclosed on the U.S. Pat. No. 5,859,527. In this case, the accelerated phosphorescence fluorescent material hereof refers to a phosphor material which internally stores part of radiation energy of a radiant ray such as an X-ray, $\alpha$ ray, $\beta$ ray or $\gamma$ ray for a certain period of time or a long period of time when the radiant ray is irradiated onto the accelerated phosphorescence fluorescent material and discharges a stored energy as an accelerated phosphorescence fluorescent light. The type of radiant ray whose energy can be easily stored, the wavelength of a excitation light which is prone to emit an accelerated phosphorescence fluorescent light and the wavelength of the accelerated phosphorescence fluorescent light to be emitted differ with the type of the phosphor material.

FIG. 2 is shows an example configuration of the system using the accelerated phosphorescence fluorescent panel.

The system shown in FIG. 2 is an example of a photographing unit and a reader unit which are independently arranged.

In the photographing unit 10, an X-ray generated by an X-ray generating part 11 is irradiated to a subject 12 standing on a photographing stand 14 and the X-ray 13 which has passed through the subject 12 is irradiated to the accelerated phosphorescence fluorescent panel 15, thereby an X-ray image of the subject 12 is cumulatively stored on this accelerated phosphorescence fluorescent panel 15. Hereinafter, the accelerated phosphorescence fluorescent panel may be referred to as "imaging plate" or "IP" for simplicity.

After the photography has been carried out as described above, the accelerated phosphorescence fluorescent panel 15 is taken out from the photographing stand 14 and set in the panel inserting part 21 of the reader unit 20. In this case, the accelerated phosphorescence fluorescent panel 15 can be set in a magazine. If the accelerated phosphorescence fluorescent panel 15 which should be set in the panel inserting part 15 is set in the magazine or the cassette, the panel 15 is transferred along the transfer passage 22 after it has been taken out from the magazine or the cassette, the X-ray image cumulatively stored in this accelerated phosphorescence fluorescent panel 15 is read in the reading part 23, and image signals are generated therefrom. The configuration of this reading part 23 is described in the following. Image signals generated by this reading part 23 are entered into an image processing part 25 through a signal transmission path 24, whereby appropriate image processing such as frequency emphasis processing is given to image signals, and further entered into an image displaying part 27 through a signal transmission path 26, then the X-ray image of the subject 12 is displayed, for example, on the CRT display screen. In place of the image displaying part 27 for displaying the image obtained or together with this image displaying part 27, an image recording unit such as a laser printer, not shown, can be provided to reproduce and record an X-ray image, for example, on a silver halide film and obtain the X-ray image as a hard copy through developing treatment.

The accelerated phosphorescence fluorescent panel 15 which is read by the reading part 23 is transferred to an erasing part 29 along the transfer passage 28. This erasing part 29 irradiates an erasing beam onto this accelerated phosphorescence fluorescent panel 15 to erase the energy (visual persistence or after image) which remains on the accelerated phosphorescence fluorescent panel 15. The accelerated phosphorescence fluorescent panel 15 on which this after image is erased is transferred to the panel takeout part 31 along the transfer passage 30, taken out from the reader unit 20 and set on the photographing unit 10 for repeated use.

FIG. 3 shows a configuration example of the other system using the accelerated phosphorescence fluorescent panel. In FIG. 3, the components of the system corresponding to those of the system shown in FIG. 2 are given the same numbers and only the differences are described.

The system shown in FIG. 3 is provided with a stand-alone type photographing unit 40 in which the photographing stand 14 of the photographing unit 10 and the reader unit 20 are arranged integrally. Photography is carried out using the accelerated phosphorescence fluorescent panel 15 set in the photographing part 31 and the accelerated phosphorescence fluorescent panel 15 is transferred to the reading part 23 and read therein, then transferred to the erasing part 29 along the transfer passage 28 for erasing the after image, and further set again in the photographing part 31 along the transfer passage 30 for following photography.

FIG. 4 shows a configuration example of the reading part 23 shown as a block in FIGS. 2 and 3.

The accelerated phosphorescence fluorescent panel 15 on which the X-ray image is cumulatively stored is transferred (sub-scanned) by transfer rollers 100 in a direction indicated with arrow Y in the reading part shown in FIG. 3.

During this transfer (sub-scanning), a laser beam 102 emitted as an excitation beam from the laser beam source 101 is repeatedly reflection-deflected by a scanner 103 such as a galvanometer mirror or a polygon mirror, passes through a beam shape correcting optical system 104 such as a fθ lens and is irradiated onto the accelerated phosphorescence fluorescent panel 15 after having been reflected by the reflection mirror 105, thereby the accelerated phosphorescence fluorescent panel 15 is repeatedly scanned (main scanning) by the laser beam 102 in the direction of arrow X. An accelerated phosphorescence fluorescent light which bears an X-ray image cumulatively stored on the accelerated phosphorescence fluorescent panel 15 is emitted from respective scanning points. This accelerated phosphorescence fluorescent light is condensed by a condenser 106 such as an optical fiber array or the like, guided into a photo-multiplier tube 108, which cuts off the excitation light and transmits the accelerated phosphorescence fluorescent light passes, through an optical filter 107 and converted to electric signals. The accelerated phosphorescence fluorescent light can be directly received by providing, for example, a CCD optical sensor to which an optical filter which transmits only the accelerated phosphorescence fluorescent light at the front side without using the condenser 106.

Electric signals obtained through the photo-multiplier tube 108 are converted to digital image signals S by an A/D converter 110 after having been logarithmically amplified by a logarithmic amplifier 109. A sampling timing in this A/D converter 110 is controlled by the A/D conversion control part 113. These digital image signals S are directly stored in a storage medium 112 such as a magnetic disk or an optical disk after they have been stored temporarily in a frame memory 111 or without passing through the frame memory 111. Subsequently the image signals stored in this storage medium 112 are read out and entered into the image processing part 25 shown in FIGS. 2 and 3.

It is recognized that, in the system using this accelerated phosphorescence fluorescent material, an energy of the radiant ray to be irradiated onto this accelerated phosphorescence fluorescent material and a quantity of light of the accelerated phosphorescence fluorescent light to be emitted from irradiation of the excitation light are proportional to each other in a wide range of energy, a ratio can be changed in accordance with the quantity of excitation light. Therefore, a radiation image which will not be affected by a change of an exposure dose of the radiant ray can be obtained and photographic errors can be reduced. In a system for obtaining X-ray images of a human body, the exposure dose of the radiant ray to a human body can be reduced.

Both a system using the film reader and a system using the accelerated phosphorescence fluorescent material are able to obtain digital image signals and therefore these systems are featured in that less space is required for storage and information retrieval is easy and furthermore image processing can be carried out.

Problems to be Solved by the Invention

Along with an increase of cases suffering from lung cancer in recent years, it has been demanded to merely implement in a simple way not only generation and display of radiation images but also a method of determination of a malignant tumor and a benign tumor from radiation images or accurate detection of a 3-dimensional position of the tumor. When the presence of a disease is suspected on an image obtained from simple photography, a front view photography and a side view photography or, if required, a perspective view photography have usually been carried out and, in addition, dorsoventral and ventrodorsal photography have been carried out to detect a position of an affected portion. Thus, means has been carried out for estimating the position of the affected position of a case from slight positional deviations to be found on a plurality of images which necessarily form a magnified photography and this means has been sufficient only for detection of the affected position. However, those who are able to practise this means need be physicians having sufficient knowledge and moreover high level medical knowledge and experience are required to know what the position of the disease such as a tumor which has been obtained means. In other words, it is important to know what types of blood vessels, bronchi, etc. are present at that portion and therefore physicians build up a 3-dimensional structure in their heads and estimate the condition of the disease. In addition, the physicians estimate the nature of tumor as to whether it is located near a pulmonary trunk or a pulmonary vein and reconfirm the accurate position of the affected portion and diagnose more accurately a true nature of the tumor through tomography, CT scan or contrast photography.

These diagnostic techniques have been established and do not include remarkable disadvantages. For detecting the affected portion more precisely, however, it has been attempted to display a 3-dimensional blood vessel structure on the CRT by using a calculator graphic technology based on the information from angiography (DSA), tomography or CT scan. This technology enables to indicate a position of the blood vessel nearby which the tumor in question is located and therefore the estimation accuracy of the nature of tumor has been improved. However, this technology is disadvantageous in that the estimation of an affected portion based on interpolation from information which is not 3-dimensionally continuous is only the estimation, a great deal of calculations are required and, if a photographic interval is inappropriate, the difference will be large. Those equipment for tomography and CT are originally expensive.

In addition, the inventor and others found a considerable problem as described below as a result of studies on twodimensional radiation images, which can be 3-dimensionally viewed as a stereoscopic vision, by photographing the same subject in directions which deviate from one another as far as an angle corresponding to a parallax with respect to thoracic radiation images. Specifically, since the chest behaves as the heart beats, the relation of 3-dimensional positions is disordered during two or more times of photography for which a position of an X-ray bulb for stereoscopic vision has been changed This is the same with the X-ray CT and the MRT which are required for many hours in photography or measurement and an artifact due to respiration and physical motion is unavoidable. In simple X-ray photography or contrast photography, the position deviation can be substantially reduced by replacing the radiation sensor within an extremely short period of time. In photography for obtaining, for example, two images within 0.1 second, the above problem as to the positional deviation can be largely solved by photographing the images within one or two seconds in synchronization with respiration, electrocardiography or pulse waves. On the other hand, in such photography, 3-dimensional positions could not be completely aligned due to the presence of physical motion. Though this is remarkably observed particularly in obtaining stereoscopic thoracic radiation images, the pulsation of blood is unavoidable as well as in the chest with a further problem of physical motion in photography of radiation images of animals including human bodies and therefore the above problem is common to the radiation images of all parts of a body. This is clearly the same with the subjects, which behave quickly in a short period of time, other than human bodies.

SUMMARY OF THE INVENTION

A first object of the present invention made in view of the above is to provide a novel method for generating 3-dimensional radiation images.

A second object of the present invention is to provide a method for generating 3-dimensional radiation images capable of solving the above problems and completely aligning 3-dimensional positions.

Means for Solving the Problems

A method for generating 3-dimensional radiation images according to the present invention is characterized in that at least one 2-dimensional radiation image of a subject carried by the radiant ray which has passed through the subject is obtained by irradiating the radiant ray from a plurality of positions, which differ from one another, toward the subject, 2-dimensional pixel data which denote pixel values at respective points on the 2-dimensional radiation image by repeatedly scanning the image in a main scanning direction which intersects a sub-scanning direction while sequentially moving in the specified sub-scanning direction on this 2-dimensional radiation image, and 3-dimensional pixel data which denote the pixel values corresponding to 3-dimensional points inside the subject based on the 2-dimensional pixel data are obtained.

Hence it is preferable to use one 2-dimensional radiation image obtained by simultaneously irradiating the radiant ray from a plurality of respective different irradiating positions toward the subject as the above-described 2-dimensional radiation image. In the case that the subject is stationary or the behavior of the subject is ignorable, one 2-dimensional radiation image obtained by sequentially irradiating the radiant ray from a plurality of respective different irradiating positions toward the subject, or a plurality of 2-dimensional radiation images obtained by sequentially irradiating the radiant ray from a plurality of different respective irradiating positions toward the subject with respect to radiant irradiation from respective positions can be used.

If 3-dimensional pixel data (3-dimensional image) of the whole subject are not required, it is preferable to irradiate the radiant ray to the subject which is covered by a radiation shield except for a part with which 3-dimensional pixel data is desired.

It is also preferable to set a plurality of the above described positions so that a line connecting a plurality of above-described irradiating positions extends in a direction corresponding to the main scanning direction or the sub-scanning direction on the 2-dimensional radiation image.

Otherwise, if the extending direction of the line does not correspond to the main scanning direction or the sub-scanning direction, the 2-dimensional image can be rotated based on the 2-dimensional pixel data to make these directions correspond each other. In this case, the radiant ray can be irradiated to the subject while markers are attached to the subject to recognize the images of a plurality of markers obtained on the 2-dimensional radiation image, an angle formed by the line between the plurality of images and one of the main scanning direction and the sub-scanning direction can be obtained, the plurality of above-described irradiating positions can be adjusted so that the angle is zero or the 2-dimensional radiation image can be rotated.

For obtaining 3-dimensional pixel data based on 2-dimensional pixel data, it is preferable to irradiate the radiant ray to the subject from the plurality of irradiating positions, set the maximum distance $\Delta$ max between the plurality of points formed on the 2-dimensional radiation image by the radiant ray which has passed through the subject, obtain a plurality of scanning points on the 2-dimensional radiation image corresponding to respective points in the subject within the maximum distance $\Delta$ max, and further obtain the 3-dimensional pixel data based on the 2-dimensional pixel data obtained from the plurality of scanning points.

For setting the maximum distance $\Delta$ max, it is preferable to irradiate the radiant ray to the subject the irradiation side of which markers are attached to recognize a plurality of images of markers obtained on the 2-dimensional radiation image, and set the above-described maximum distance $\Delta$ max based on the distance among the plurality of images.

Otherwise, if a thickness of the subject in a radiant ray penetrating direction can be estimated in advance, the maximum distance $\Delta$ max can be set without photographing the markers.

For obtaining the above-described plurality of points present within the maximum distance $\Delta$ max, a method for finding the plurality of points corresponding to the specified points in the subject can be used by recognizing a plurality of points having the same pixel value, which permits a specified error, within the maximum distance $\Delta$ max as a plurality of candidate points corresponding to the specified points in the subject and the continuity of these candidate points on the 2-dimensional radiation image.

For recognition of the above continuity, it is preferable to obtain a representative pixel value (for example, the minimum value and the maximum value) of a plurality of pixels within a specified area in the ambiance of each pixel on the 2-dimensional radiation image as each base pixel value of each corresponding pixel and recognize the above-described continuity of points based on the difference between the original pixel value and the base pixel value of each corresponding pixel.

For obtaining a plurality of points on the 2-dimensional radiation image corresponding to respective points in the subject, it is preferable to carry out smoothing of the 2-dimensional radiation image based on the 2-dimensional pixel data and a different appropriate processing for each area on the 2-dimensional radiation image is preferable as this smoothing.

Though, in the present invention, a method of using the 3-dimensional pixel data obtained as described above is not limited, the main method of utilization includes, for example, displaying of a desired tomographic image of a subject generated based on the 3-dimensional pixel data, an image obtained from projection of a subject in a desired direction based on the 3-dimensional pixel data, an image of a subject, which is a live body from which at least part of the bone thereof is removed and projected in a desired direction, a pixel value of a bone of a live subject obtained based on the 3-dimensional pixel data or a plurality of 2-dimensional radiation image of a subject which is projected in directions which differ from one another as much as an angle corresponding to a parallax and generated based on the 3-dimensional pixel data.

In the present invention, one of, for example, a silver halide film and an accelerated phosphorescence fluorescent material can be used as a radiation sensor to obtain the 2-dimensional radiation image. In addition, an II camera or a CCD can be used as the radiation sensor.

A method for generating 3-dimensional radiation images according to the present invention is such that a radiation image obtained from a plurality of different irradiating positions is simultaneously or sequentially recorded on at least one, for example, accelerated phosphorescence fluorescent panel or silver halide film, 2-dimensional pixel data is obtained by reading this radiation image, a plurality of points corresponding to 3-dimensional points in a subject are obtained on a radiation image based on the 2-dimensional pixel data obtained and 3-dimensional pixel data of 3-dimensional points are obtained from the 2-dimensional pixel data of the plurality of points, thereby a 3-dimensional radiation image can be obtained without requiring special photography including time-consuming work such as binary coding of pixel data obtained from conventional angiography to obtain 3-dimensional information of blood vessels and plural times of tomographic photography to obtain 3-dimensional image.

Since a method according to the present invention allows to generate a 3-dimensional radiation image based on a single 2-dimensional radiation image obtained by simultaneously irradiating the radiant ray from a plurality of irradiating positions, an artifact due to movement of a subject can be avoided even in photography of an active subject a 3-dimensional radiation film of the subject at an instant timing of photography can be obtained.

For a 2-dimensional radiation image (original image) according to a method of the present invention are used two 2-dimensional radiation images obtained by a method (hereinafter referred to as the "two-image system") for obtaining two 2-dimensional radiation images by sequentially irradiating the radiant ray a plurality of times (typically two times, as described in the following description) while changing the angle of irradiation as usually carried out or one 2-dimensional radiation image obtained by a method (hereinafter referred to as the "one-image system") for obtaining one 2-dimensional radiation image on which images obtained with the radiant ray irradiated simultaneously or sequentially are superposed by simultaneously or sequentially irradiating the radiant ray from a plurality of positions with different angles (hereinafter described as two positions in a typical example). Difference between simultaneous irradiation and sequential irradiation of the radiant ray from two positions in the one-image method is a difference between an image on which completely registered 2-dimensional radiation images are superposed in a case of an active subject, that is, therefore a 2-dimensional radiation image from which a 3-dimensional image free from the artifact is obtained and an image on which 2-dimensional radiation images including slight positional deviation are superposed, that is, therefore a 2-dimensional radiation image from which a 3-dimensional image including slight artifact is obtained. A difference between the one-image system and the two-image system is a difference between that one 2-dimensional radiation image includes 3-dimensional image information and that only combination of two 2-dimensional radiation images may include 3-dimensional image information and therefore there is no inherent difference between these two systems.

The following describes a basic idea (precondition) for accomplishing the present invention. Though the basic idea is the same both with the one-image system and with the two-image system, the image processing method in the latter system is slightly more complex than the former system and the image processing method of the former system is involved in the method of the latter system. For this reason, the latter system is mainly described and only differences of the former system from the latter system are described below.

First, a radiation image is a projection image which primarily includes all information of a subject. However, in the case that a subject is thick in a radiant ray penetrating direction and a certain structural object, which originally exists in the subject, is far smaller than the resolution of the sensor or negligibly included in noise due to lack of radiation dose which results in scattering of the radian ray, the image of this structural object does not clearly appear on the projection image and therefore the information of such object is originally ignored in the present invention. For example, it is not expected to obtain the information of thin blood vessels and bronchi which are deemed initially ignorable.

Second, for simultaneous irradiation of the radiant ray to a subject from two directions, the radiant ray is mirradiated in parallel to a read line (line) or a row so that two projection images of an extremely small object in the subject exist on the same line when digital images are to be obtained regardless of the type of the radiation sensor. Though the results of image processing are the same with the irradiation in parallel to the line and the irradiation in parallel to the row, the following describes the results in the case of irradiation in parallel to the line for convenience in processing. With this, 3-dimensional information of such micro structural object is obtained from processing of the image information in one line, or between a pair of lines in the case of the two-image system. In the present invention, this precondition is not absolutely required and, if this condition cannot be established, the image can be rotated to meet this condition.

For example, in FIG. 5 theoretically showing the coordinates for photography, a projection image of a micro structure at one point in a subject appears at two positions XAR and XAL on the same line. Whether a pair of pixel values SAR and SAL are of a pair of pixels can be easily determined by selecting the pixels with which a difference between absolute values of SAR and SAL is least, that is, for example, pixels with which $(SAR-SAL)^2$ is smaller.

3-dimensional coordinates of point A are easily obtained from XAl–XAR, distance 2c between two X-ray bulbs and distance H between the center line of two X-ray bulbs and the sensor, and a difference between a radiation absorption of the structural object A and a radiation absorption of the ambiance or a value in proportion to this difference can be easily obtained.

Specifically, the 3-dimensional positions of the structural object A can be easily calculated by using equations (1), (2) and (3).

$$x = c(XL-XR)/(2c+XL-XR) \quad (1)$$

$$z = H(XL-XR)/(2c+XL-XR) \quad (2)$$

$$y = HzY/(H-z) \quad (3)$$

The radiation sensors hereof include all radiation sensors such as silver halide film, II camera, accelerated phosphorescence fluorescent material and semiconductor sensors which have been available or will be available in the future regardless of their types. However, if the silver halide film is used as a radiation sensor, the image of the silver halide film should be converted to digital signals by a film digitizer.

Third, if an angle between two irradiation directions of the radiant ray is relatively small, the quantity of absorption of the radiant ray (=thickness of the subject×absorption ratio× radiation dosage at the corresponding point) based on the shape and the radiation absorption ratio of structural object A is not varied by the angle as far as within the range of difference and therefore it is assumed that two signals from the same structural object have the same pixel value component. The pixel value component hereof is defined as a degree of effect of a micro structure (micro cubic structure: boxel) which shares the pixel value of the projection pixel× the pixel value. Though this assumption depends on the space resolution, the density resolution and the size of one pixel, it is sufficiently available for the objects of the invention since most structural objects of a human body such as blood vessels, tumor and ribs are originally round-shaped in their edge parts.

3-dimensional information is obtained from the image information in one line according to the above three preconditions. For example, as shown in FIGS. 6 and 7 which typically show a pixel value string on a certain line, 3-dimensional coordinates and the quantity of radiation absorption of respective structural objects can be obtained even if a number of structural objects with different pixel values exist. FIG. 6 shows the case of simultaneous radiation in the one-image system and FIG. 7 shows the case of radiation in the two-image system.

However, when the image information of structural object B which shows the same pixel values as those of two image information from the same structural object A exists in the same line, it is assumed that structural object A cannot be discriminated from structural object B. As shown in FIG. 8, when only two of four image information exists within the range of the maximum distance Δmax which can be calculated in advance from thickness Zmax and distance H between interval 2c of the X-ray bulbs and the sensors by the equation (4), the image information of the same structural object A does not exceed this maximum distance Δmax and therefore these two structural objects A and B can be discriminated. The pixel within the upper range of Δmax of two ranges of Δmax shown in FIG. 9 will be paired with one of pixels in the lower range of Δmax.

$$\Delta max = 2c\, Zmax/(H-Zmax) \quad (4)$$

However, when three or more pixels with the same pixel value exist in the range of the maximum distance Δmax, the structural objects carrying these pixels cannot be discriminated by simple comparison of pixel values on the same line. The maximum distance Δmax can be reduced to make such case difficult to occur. In other words, the maximum distance Δmax can be reduced by reducing 2 c/H and therefore it requires less efforts to retrieve the pixels with the same pixel value. However, if the maximum distance Δmax is excessively small, the resolution will deteriorate and an appropriate value is therefore necessary. The value H cannot be so large in general photographic rooms and therefore an appropriate value c is recommended. However, this problem cannot be completely solved by these selective measures. A more complete solution is described below.

When a subject is equal to or larger than the sensor in dimensions, there may be only one information of the same structural object on one line with respect to pixels of the end surface of the sensor. Accordingly, it is impossible to obtain the 3-dimensional positions of that structural object. On the contrary, the sensor should b arranged so that only information from one radiation source exists at the left-side end or the right-side end of the line in order to avoid such deficiency. Specifically, if it is determined in advance which part of the subject is desired as a 3-dimensional image, the irradiation field of the radiant ray on the subject is limited so that the radiant ray is irradiated only onto the selected part as described above and an image is scanned by a radiation sensor with a larger area than the irradiation field of the radiant ray, only the information from the left-side or right-side radiation source must exist at the left-side end or the right-side end of the line and a kind of boundary condition for analysis by utilizing the above settings can be obtained.

Originally, the main object of this system is to obtain the 3-dimensional coordinates of an affected part of a subject of which a photographing position has been known in simple photography and therefore the irradiation field is limited to, for example, approximately ¼ of a half size. If a material such as a lead plate which shuts off the radiation is arranged so that the radiant ray is irradiated only to the affected part of the subject, the information obtained by irradiation of the radiant ray from one X-ray source certainly appears in the pixels in the range of the maximum distance max of the left-side end surface for processing the image (upper side of FIG. 10) as shown in FIG. 10 and the information to be obtained by irradiation of the radiant ray from the other X-ray source does not exist. Therefore the radiation image must be extremely simplified for analyses. This is reversed for the right-side end of the subject. Though the limitation of the irradiation field is not an essential requirement for the present invention, the analysis can be facilitated and the reliability of analysis can be improved by limiting the irradiation field as described above and sequentially analyzing pixel information from the right-side or left-side end of the line. If the subject is far smaller than the sensor, there always exists the image information to be processed as being to be paired with the image information in the range of Δmax of the adjacent part and therefore the analyses will be further easier. Though the resolution in the direction of depth is more improved as the size of one pixel is smaller, the number of pixels to be processed will be immense to result in the necessity of increasing the memory capacity and the calculation time and therefore, for the purpose of the present invention, it is significant to limit the number of pixels to the least required for diagnosis.

In addition, the following describes the basic preconditions for attaining the present invention.

Fourth, in the case that there are many same pixel values, which cannot be discriminated on one line, within the range of the maximum distance Δmax due that the processing of images of a plurality of lines is utilized to determine the continuity and branching of the structural object and in the case that the projections of a plurality of micro structures are superposed on the image of one pixel, recognition of pixels will be possible. In other words, when two or more pixels having the same pixel values within the range of the maximum distance Δmax on one line form a continuous object which ranges over a plurality of lines (for example, a blood vessel), it is necessary to check as to other lines whether two or more pixels having the same pixel value exist within the maximum distance Δmax. If two or more pixels having the same pixel value do not exist in the maximum distance Δmax on the other lines, it is known that these pixels are not the image information to be paired with the previously obtained pixels and, if the pixels having the same pixel value which form a continuous object exist in the maximum distance Δmax until the image of the continuous object disappears, it can be recognized that these pixels are the image information to be paired. For example, in a case that the continuous object extends as shown in FIG. 11, a and b of (1), b and c of (3) and a and b of (4) are respectively the images to be paired c of (1) has disappeared earlier than a and b, c of (2) intersects with a and b, and a of (3) is away from the maximum distance Δmax, and therefore other continuous objects to be paired should be found for these image information as described above. In the case that a continuous object extends as shown in FIG. 12, the branch of the continuous object can be recognized according to the continuity and the pixel values of the continuous object (the pixel values are denoted by the width of the line in FIG. 12) in the meaning shown in FIG. 11.

Recognition of the continuous object or the branch of structural object can be easily implemented by general image processing approaches (refer to, for example, "Basic Image Recognition [1] and [2]", jointly written by Mori and Itakura, 1986 and 1990 Omusha Publishing Company). In general approaches for image recognition, however, the methods for recognition of continuous objects in a 2-dimensional space are mainly described. In the description of the invention, however, in addition to recognition of the continuity within the 2-dimensional plane, 3-dimensional positions (x, y and z) are obtained from the pixels to be paired and 3-dimensional positions (x, y and z) and pixel value component p are stored as, for example, (x, y, z and p) after each component value component has been calculated.

Thus, three or more having the same pixel value which exist in the maximum distance Δmax on one line can be completely discriminated by using the continuity and the change of pixel values and therefore more precise determination is possible.

In the case of the X-ray CT, a lot of angular information is theoretically obtained and therefore 3-dimensional coordinates and radiation absorption quantity or radiation absorption coefficient of a structural object can be obtained. In this system, however, 3-dimensional coordinates and pixel values can be obtained since a lot of information within the plane can be theoretically obtained.

The following describes processing of pixels which cannot be determined even by the above described recognition of the continuity.

Fifth, an X-ray image of, for example, the lung field can be considered an image of a region where a large amount of air is contained, that is, there are no blood vessels and bones and which therefore indicates a degree of absence of air. Accordingly, this means with respect to the lung field that a region which has the largest pixel value which actually exists in a certain range on one line or several lines but does not appear as the image information can be identified as a base line of the pixel value. On the contrary, the least pixel values of the mediastinal part, cardiac part and diaphragmatic part can be identified as the base line of the pixel values.

Sixth, if the overlap of two or more structural objects is projected onto a certain pixel and the pixel value is composed of the sum of radiation absorption quantities of a plurality of structural objects, the number of such overlaps shall be limited. For example in the lung field, it is assumed that the overlapping structural objects are two ribs, four defects and one abnormality, seven or less objects in total. Though the number of overlaps can clearly be 5 or 10 and not 7, calculation will be much easier by determining the number of overlaps to either of these numeric values. This is derived from the first precondition that a structural object which does not exist as the image information is deemed absent from the beginning. Accordingly, the structural objects can be deemed overlapped when the sum of a plurality of pixel values is equal to the pixel value even though the same pixel values do not exist in the range of the maximum distance Δmax. For resolving the sum of a plurality of pixel values into respective pixel values, it is necessary to solve as many simultaneous equations as the number of overlaps and, in this case, calculation will be much easier if the number of overlaps is limited in advance. Though an infinite number of overlaps is assumed and the measure can be prepared since such limitation of the number of overlaps is not an essential requirement for this system, that even the pixel values in the range of difference are regarded as the overlap will bring about unnecessary complexity to the analyses.

Seventh, radiation markers such as lead pellets are attached to the subject and it is checked from the projection image of markers as to whether pixels to be paired exist on the same line in the case of the one-image system and pixels to be paired exist on the lines to be paired in the case of the two-image system to know whether two X-ray bulbs are arranged in parallel to the read line of the radiation sensors. Consequently, not only the X-ray bulbs can be rearranged in parallel to the read line and, when it is difficult to position the X-ray bulbs at the original positions, new lines to be paired can be found. Despite this is not an essential requirement of the present invention, it is an extremely important contrivance for implementing the present invention and greatly affects the accuracy of calculation of the 3-dimensional images. Though various means for measuring the maximum thickness Zmax of the subject are available, the maximum thickness Zmax can be obtained from the projection image of markers which are attached to the part with the maximum thickness of the subject.

The above-described seven preconditions and assumptions can be duly available if radiation images are carefully considered, and in the present invention 3-dimensional images are generated by using at least several preconditions and assumptions. It is clearly known that many commonsense preconditions which are not enumerated as the preconditions can be used. For example, the following preconditions can be enumerated.

(1) If it is unknown whether the information of a wide and long continuous object (such as a rib) with approximately same pixel values is the information obtained from irradiation of the left-side or right-side radiant ray, it is regarded as a simple continuous object and its shape is recognized by obtaining its edge.

(2) The pixel values are standardized by using the differences between respective pixel values and base line pixel values or the maximum and minimum values of pixel information of the subject and calculation is carried out using the pixel values after standardization.

(3) A histogram of pixel values of a continuous object is used for standardization.

(4) The width of the continuous object is reduced.

(5) Pixels of the continuous object which intersect on the original image are not paired.

(6) When ambient pixels have an approximately same pixel values and only processed pixels show specific values, the processed pixels are smoothed as pre-processing for image processing or at the same time as processing.

(7) When pixel values of pixels in the ambiance of processed pixels are small, that is, radiation dosages to these pixels and therefore the S/N ratio is small, ambient pixels have the approximately same pixel values and only processed pixels and several pixels adjacent to the processed pixels show specific pixel values, processed pixels are smoothed.

(8) Space frequency processing and gradation processing are carried out before the generated 3-dimensional image is displayed.

Particularly, standardization of pixel values greatly contributes to simplification of calculations and smoothing of pixels is an essential requirement for implementation of the present invention. Though it is a common processing, smoothing is required to eliminate uncertainty of calculation due to the effects of scattering X-ray or quantum noise. For smoothing, many approaches such as substitution of the pixel values of ambient pixels in processed pixels or substitution of a median value or a mean value are effective.

In smoothing of processed pixels having pixel values different from those of ambient pixels, unnecessary calculation can be avoided by substituting the pixel values of those pixels which show the continuity in the case that the number of pixels showing the continuity is, for example, 1 to 5 or less with the mean value of pixel values of ambient pixels other than the above-described pixels or smoothing those pixels even though the processed pixels have the continuity to adjacent pixels since the quantum noise of the radiant ray and the measuring system particularly in a pixel area where the radiation transmission quantity is small. As a pixel area where the quantity of radiation transmission is small, in the case of, for example, a thoracic image, it should be a pixel area below the bottom of the histogram showing the boundary between the lung field and the mediastinal part and the cardiac part in a curve of frequency of the pixel values of all pixels or decimated pixels of the original image.

As described above, the present invention enables to generate a 3-dimensional image with less artifact from an active subject, thereby the 3-dimensional image generated as described above can be displayed as a stereoscopic image or a tomographic image, or a density of bone can be obtained and only a part of the subject can be displayed as a stereoscopic image or a projection image. For example, a variety of merits will be available from the present invention in various medical applications such as accurate detection of an affected part, checking of the condition of the surrounding part of the affected part, general diagnosis, examination of a method of operation before execution of the operation, therapy program and so forth.

BRIEF DESCRIPTION OF THE INVENTION

Figure 16:
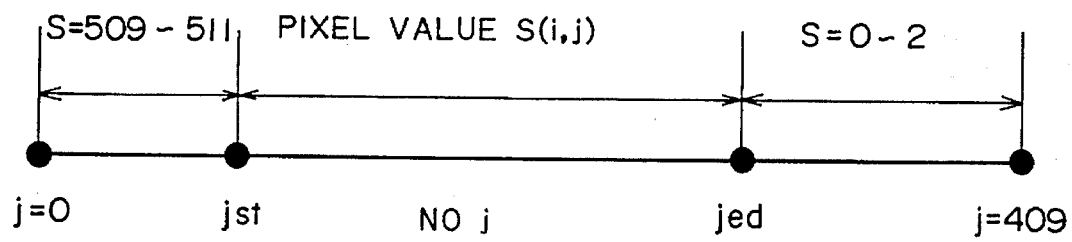
Figure 17:
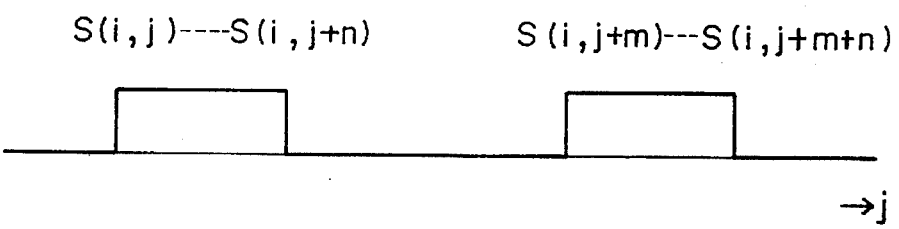
Figure 18:
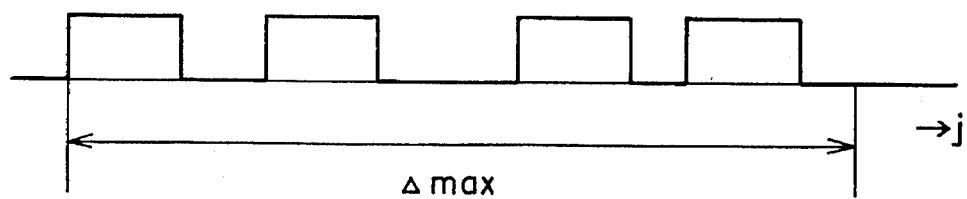
Figure 19:
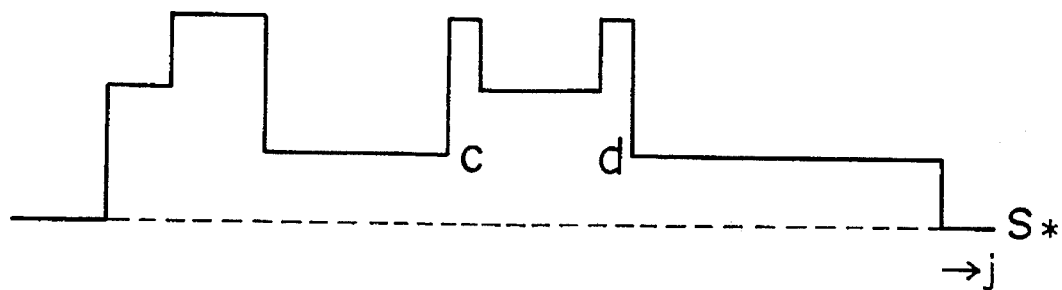
Figure 20A:
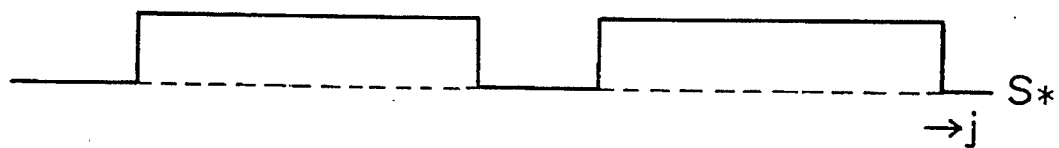
Figure 20B:
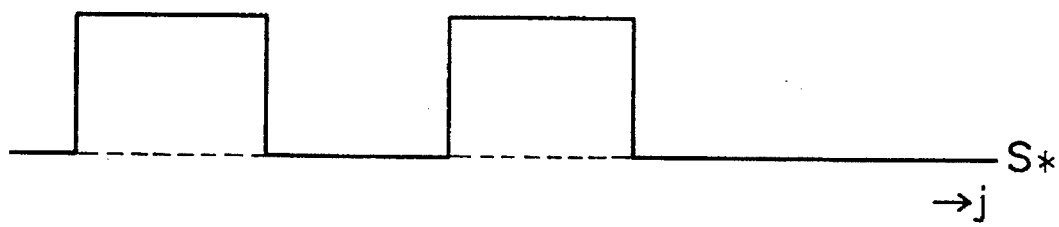
Figure 21:
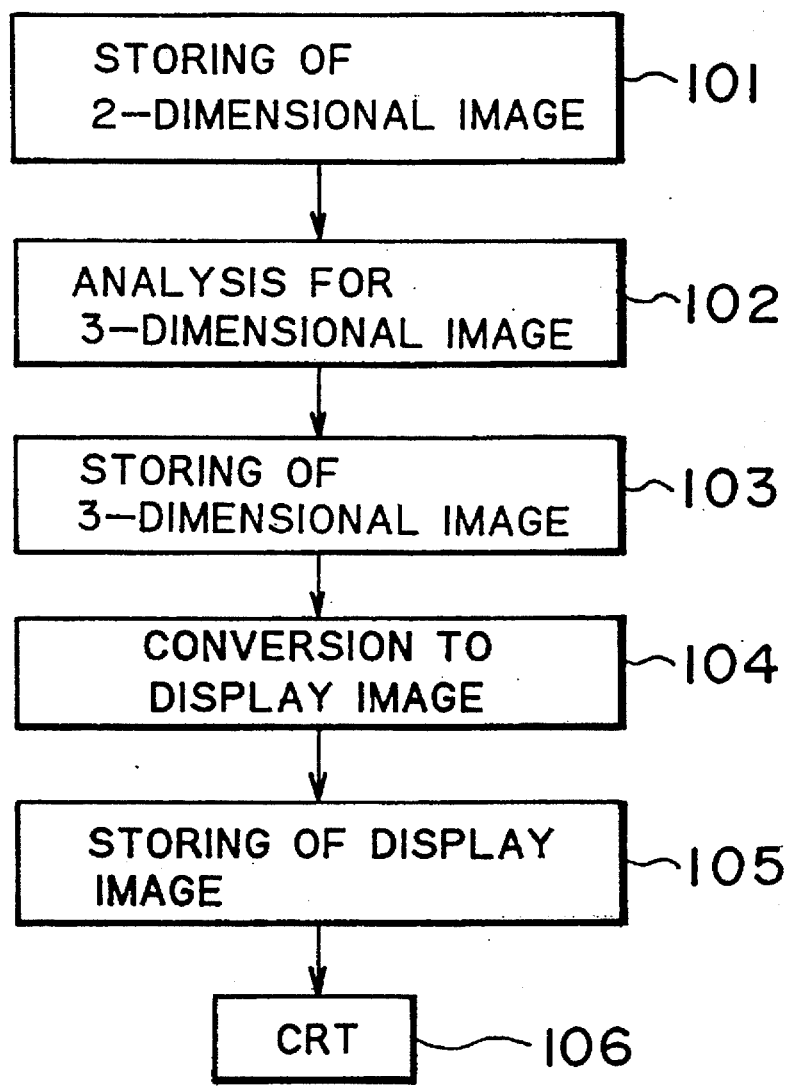

FIGS. 15A–D are illustrations showing an example of continuity composed of five pixels;

FIG. 16 is a typical diagram showing changes of a pixel value in a row direction in a line;

FIG. 17 is a typical diagram showing an example of a pair of continuous objects which are discretely distributed in a simple manner;

FIG. 18 is a typical diagram showing an example of a plurality of discretely distributed continuous objects;

FIG. 19 is a typical diagram showing an example of overlapping continuous objects;

FIG. 20A–B are illustrations showing separated continuous objects which form the example shown in FIG. 19;

FIG. 21 is an illustration showing an image processing process.

DETAILED DESCRIPTION OF THE PREFERRED EMBODIMENTS

The embodiments of the present invention are described below. For implementing the present invention, the image processing described below can be executed by using a software or a hardware.

First, an embodiment using an accelerated phosphorescence fluorescent panel is described.

Description of the Image Pickup Unit

Figure 1:
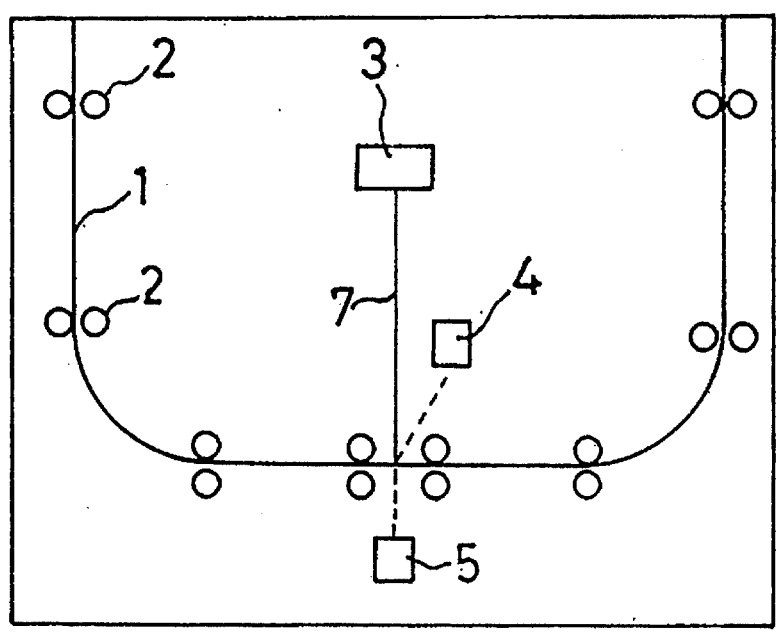
FIG. 1 is an illustration showing a configuration example of a film digitizer.
Figure 2:
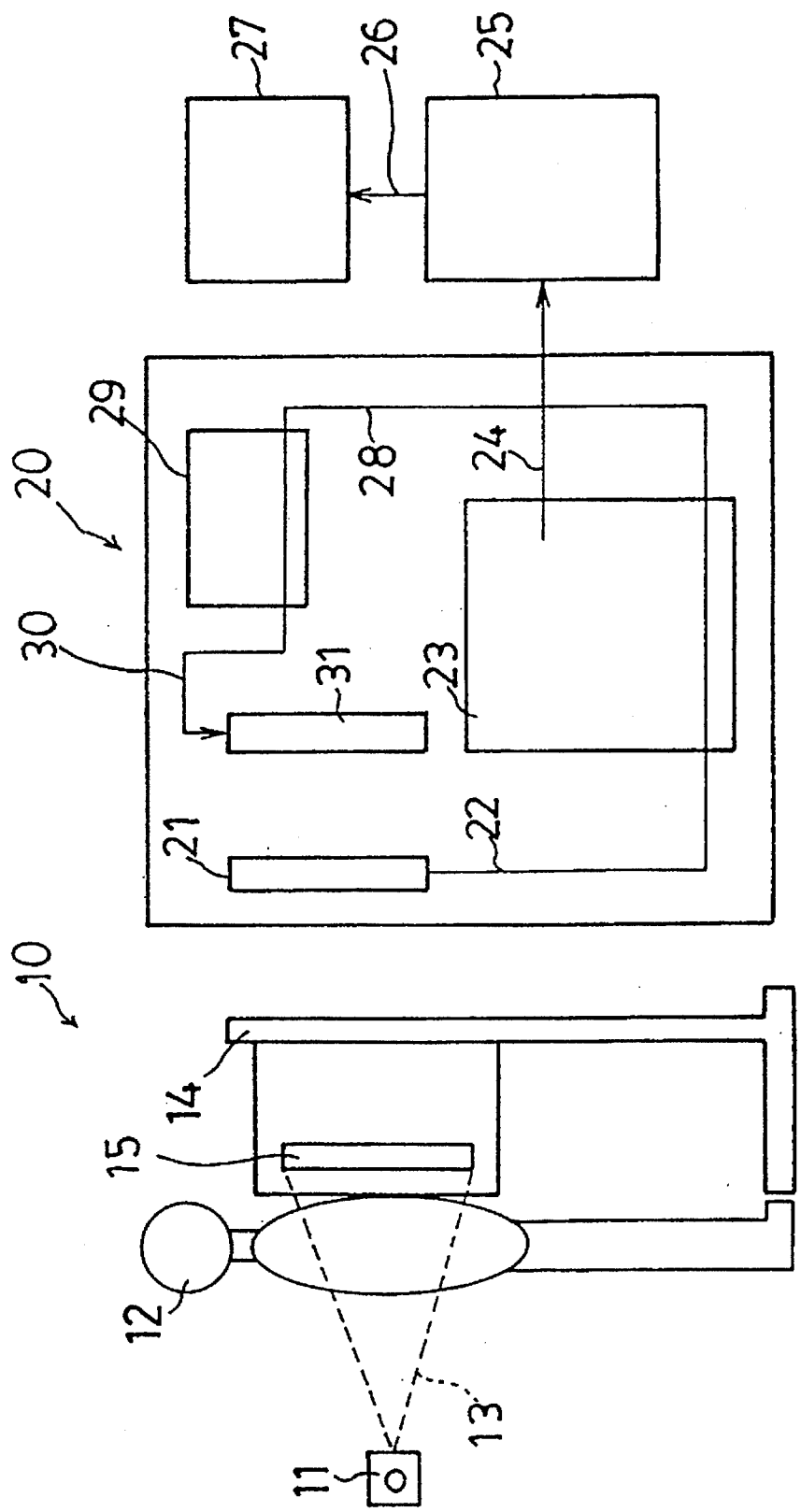
FIG. 2 is an illustration showing a configuration example of a system using an accelerated phosphorescence fluorescent panel.
Figure 3:
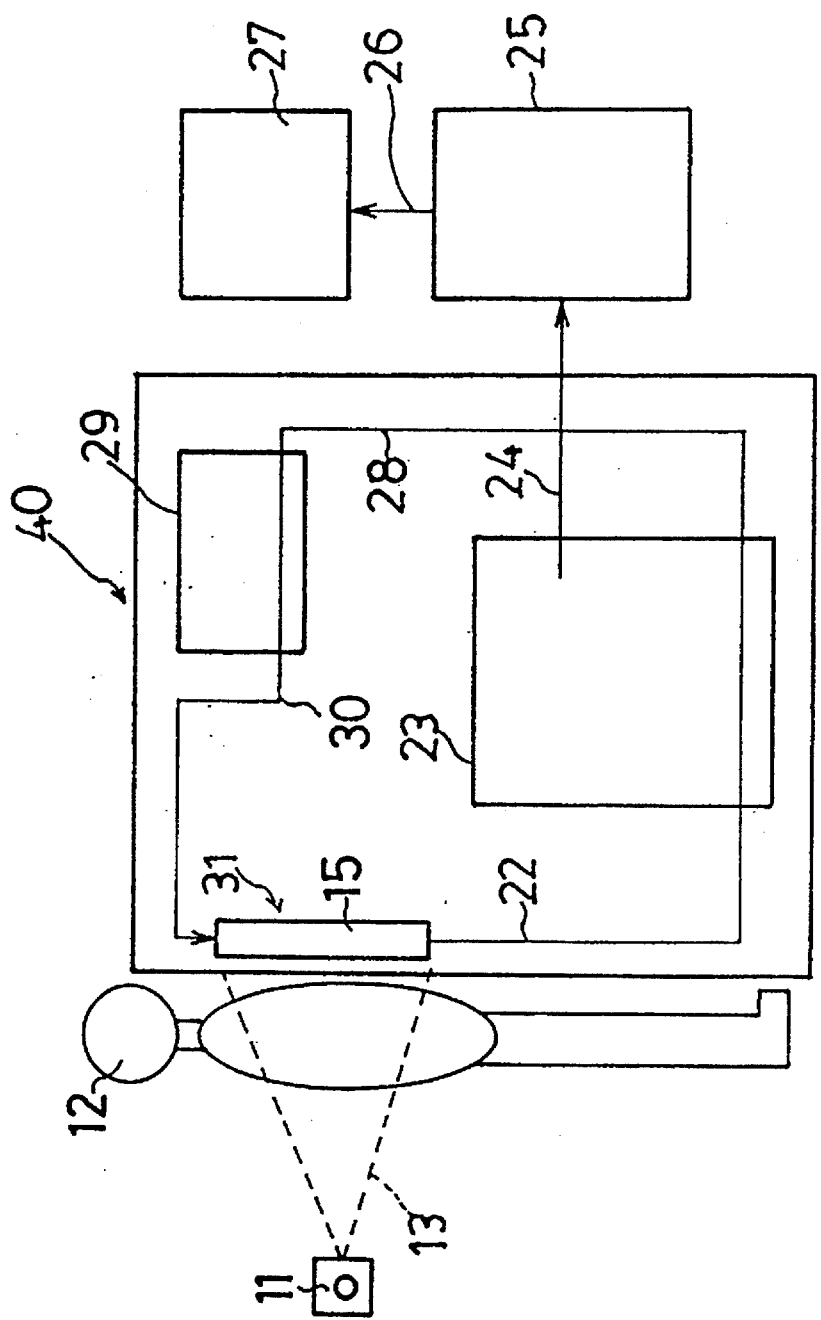
FIG. 3 is an illustration showing a configuration example of another system using an accelerated phosphorescence fluorescent panel.
Figure 4:
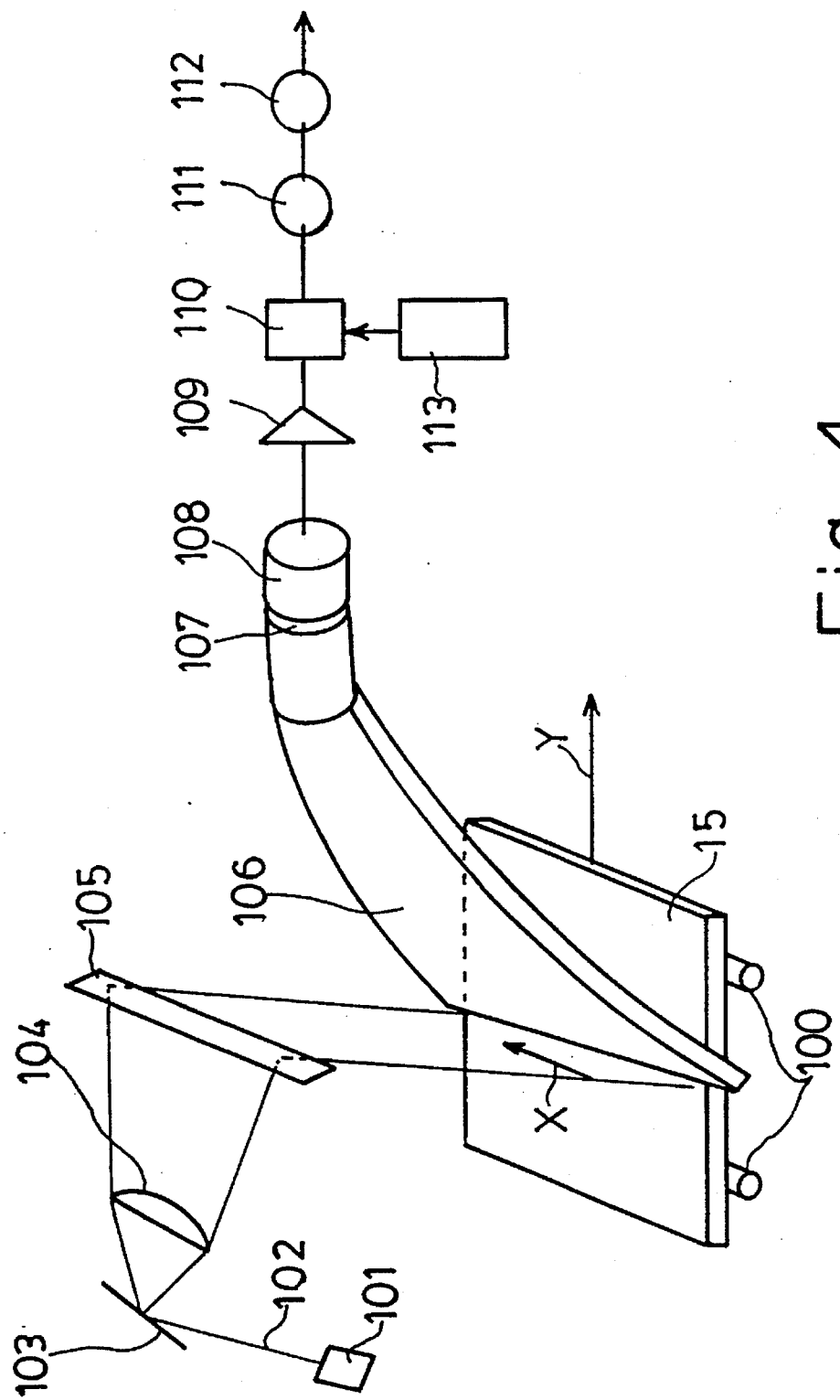
FIG. 4 is respectively an illustration showing a configuration example of a read part shown as a block in FIGS. 2 and 3.

An accelerated phosphorescence fluorescent imaging plate (hereinafter referred to as the "IP") 15 (refer to FIG. 4) of 0.3 mm in thickness and 14 inches×17 inches in horizontal dimensions which is made up by applying an acryl resin containing dispersed BaBr2:Eu powder to a glass plate is prepared as a radiation sensor, the surface of the IP 15 is scanned by a polygon mirror as a scanner 103 with a laser beam of 780 nm used as an excitation light, and a generated light of approximately 395 nm is condensed by a fiber array condenser 106 and converted to electric signals by through a photoelectric multiplier 108. Then the electric signals are converted to digital signals by the A/D converter 100 through a log amplifier 109 and temporarily stored as an image in a frame memory 11 after various compensations such as for elimination of structural noise. Then the image is stored in a recording medium 112 such as a magnetic disk, then read out from this recording medium 112 and entered into an image processing part 25 (refer to FIGS. 1 and 2), thereby space frequency processing and gradation processing are carried out. The number of pixels to be read is 4096 rows×4974 lines (approximately 20 mega pixels) for a size of 14 inches×17 inches and the size of one pixel is 86.8 μm square and the maximum pixel value is 4095 (=12 bits).

Arrangement of X-ray Bulbs

A box made of acryl having a depth of 200 mm was set as a subject in front of the photographing part (the housing of the IP installing part) and three lead pellets of 0.2 mm square were attached to the positions appropriately kept away from one another (the remotest positions from the IP) on the outside of the box with adhesive tapes. The distance between the surface of the IP to the outside of the photographing part housing is 20 mm. Accordingly, the distance from the surface of the IP to lead pellets is Zmax=220 mm.

Figure 5:
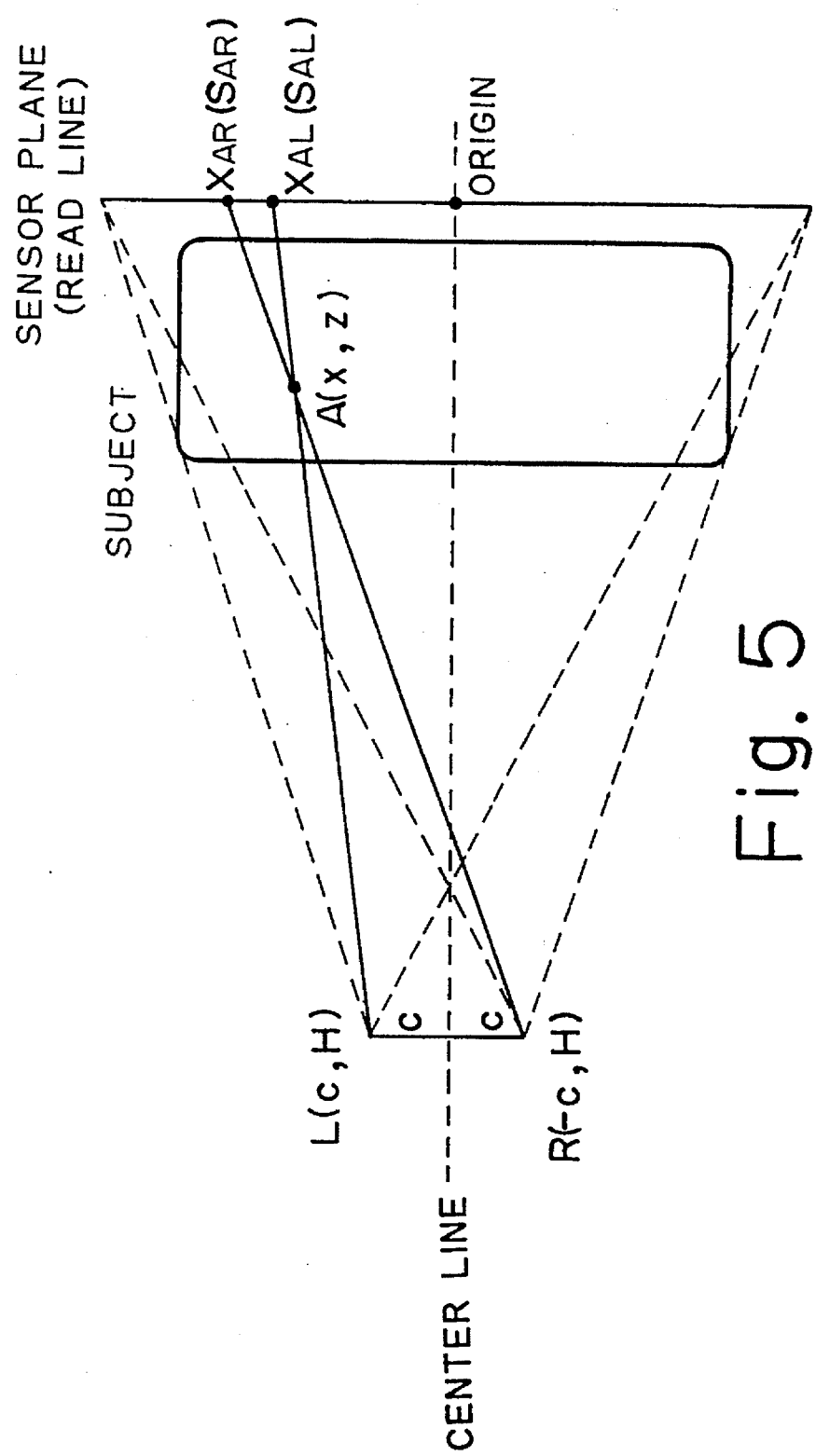
FIG. 5 is a typical illustration of the coordinates of a photographing system.
Figure 6:
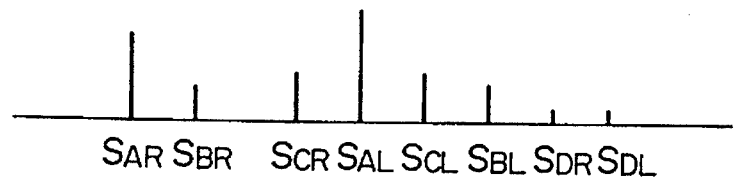
FIG. 6 is a typical diagram of a pixel value string on a line in a one-image system.
Figure 7A:
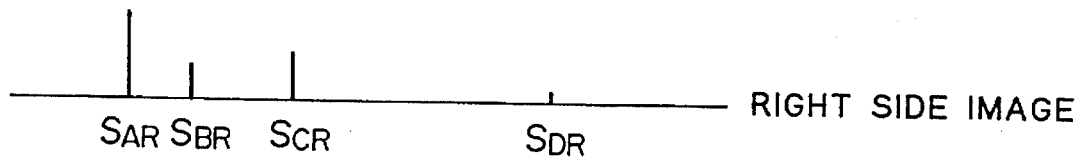
FIGS. 7A and 7B are typical diagrams of a pixel value string on a line in a two-image system.
Figure 7B:
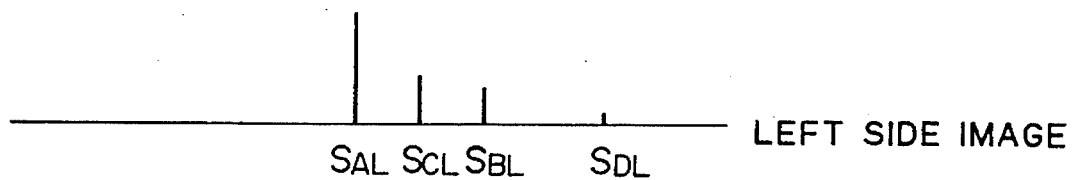
Figure 8:
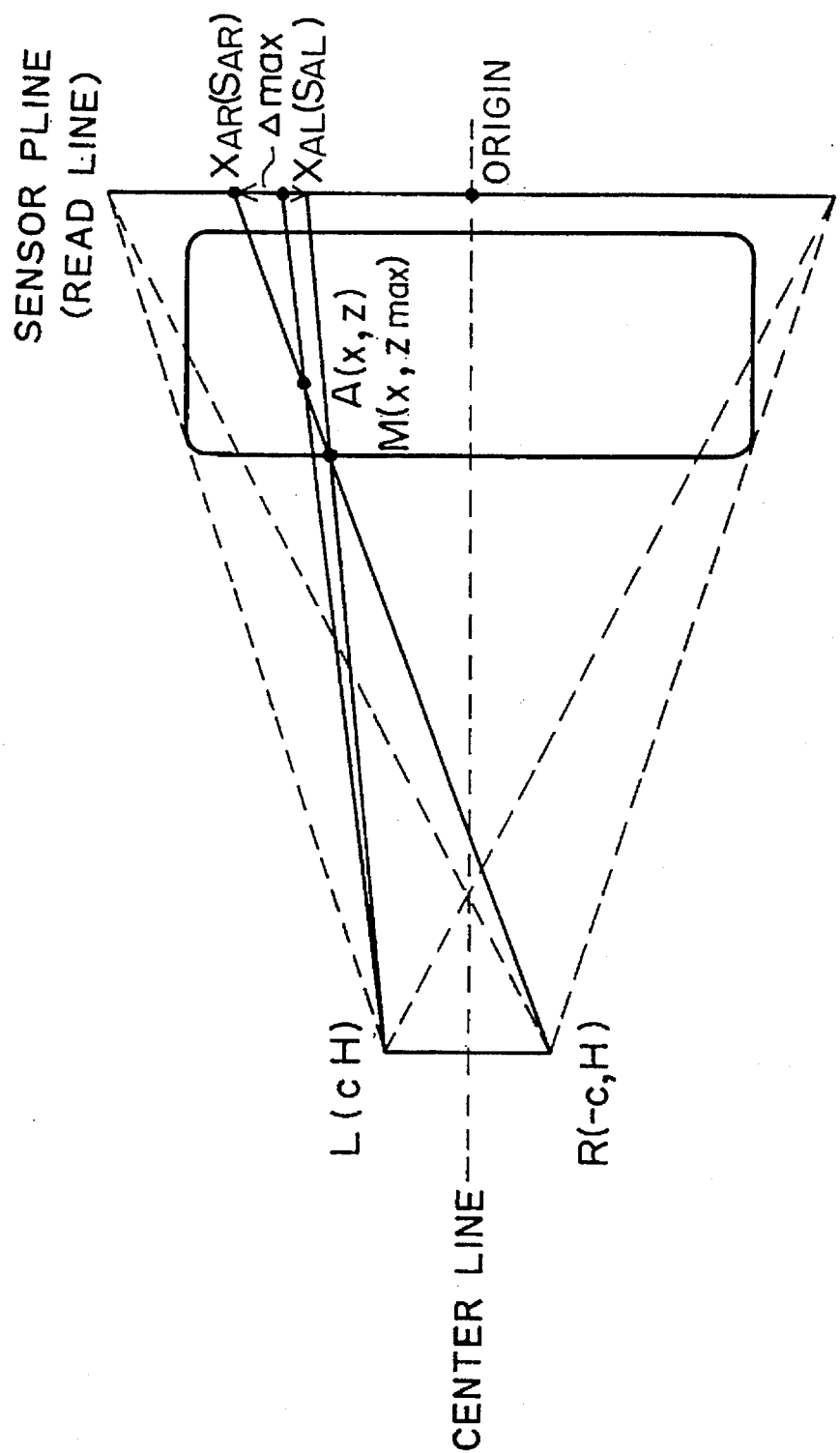
FIG. 8 is a typical illustration of the coordinates of a photographing system.
Figure 9:
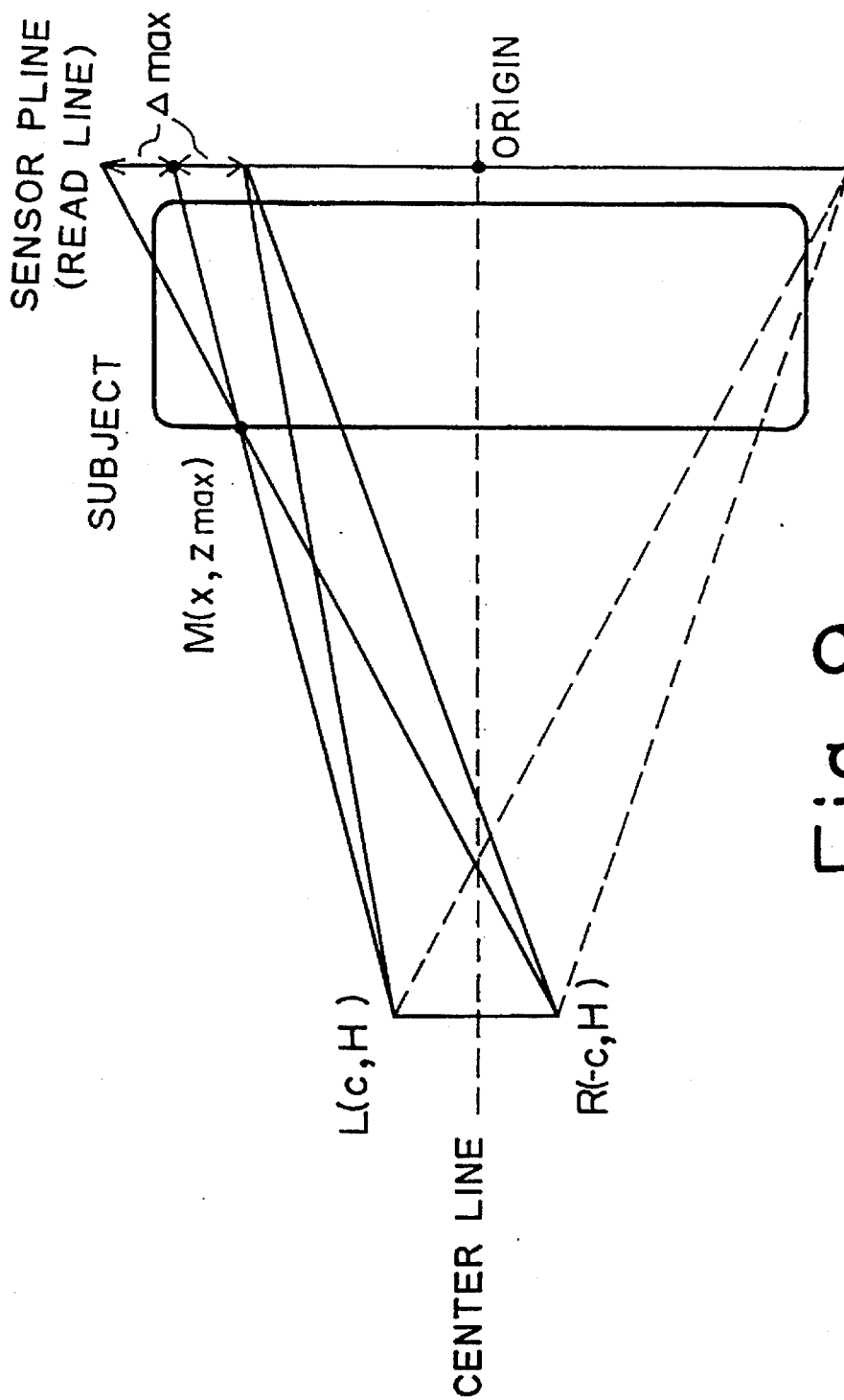
FIG. 9 is an illustration showing the maximum distance Δmax in the coordinates of the photographing system.
Figure 10:
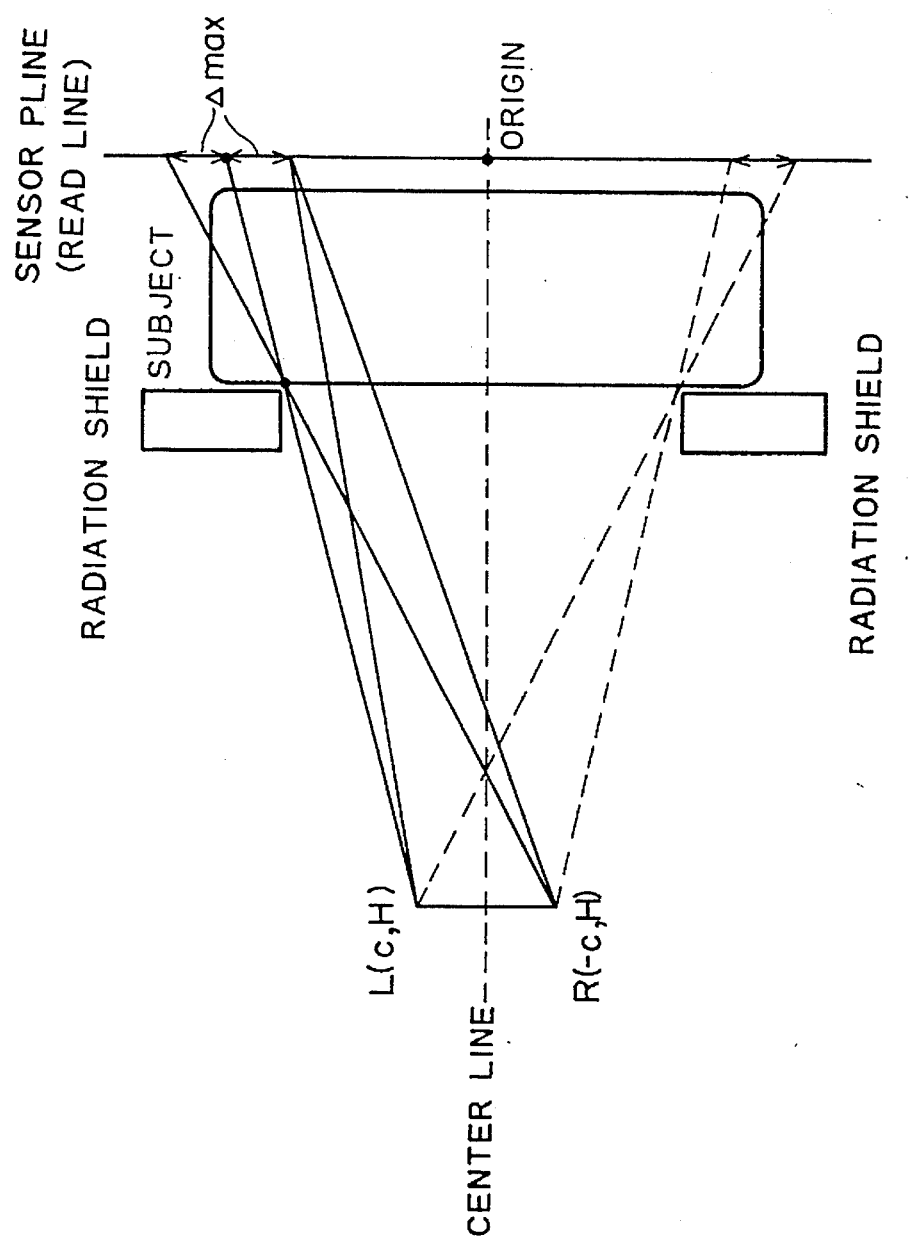
FIG. 10 is an illustration showing the relationship between the installation of a radiation shield and the maximum distance Δmax in the coordinates of the photographing system.

An X-ray bulbs was arranged at the position H=2020 mm away from the surface of the IP as shown in FIG. 5. Since only one X-ray bulb is available, it is arranged at a height of the center in the direction of height of the IP surface (2487th line as read) and the photography was carried out while shifting the position of the X-ray bulb so that the distance between the right side position and the left side position of the X-ray bulb 40 mm, that is, c=20 mm. Accordingly, the maximum distance Δmax which permits a pair of pixels is approximately 4.9 mm and the number of pixels is 57 rows. The minimum distance Δmin which permits a pair of pixels approximately 0.4 mm. As a result of separate X-ray irradiation from the right side and the left side under the condition of the bulb voltage of 100 KVP and the dosage of 1 mAs, and comparison of images which have been read, it was initially known that the images of lead pellets have deviated as long as 20 lines and the maximum distance Δmax which permits a pair of pixels was in the range of 57±10. As a result of repeating adjustment of the X-ray bulb position ten times, the images of lead pellets were observed over three lines with the same number and the maximum distance of three lead pellets appeared in the range of 57±1 showing excellent repeatability. To simplify the description, the maximum distance Δmax and the minimum distance Δmin shall be expressed as Δmax and Δmin.

Description of Image Pickup Method by One-image System

Since a human body could not be photographed in the experimental room, an image was obtained by using a human thoracic phantom (made by Kyoto Kagaku). This thoracic phantom is precisely made up with a number of blood vessels in the lung field and thin blood vessels of 2 mm in diameter provided near both ends of the lung field. The dimensions of the phantom are such that the maximum thickness is 180 mm, the maximum width including arms is 570 mm and the maximum width of the chest is approximately 380 mm.

A lead pellet was attached to the back of the phantom, the phantom was installed so that the back of the phantom was positioned at the X-ray bulb side and the center of the left-side lung was located approximately at the center of the IP and a sexual gland protector of 1.0 mm in a lead equivalent was set to cover the right-side lung field so that the right-side lung field was partly seen from the mediastinal part. As in photography of the acryl box, In the above arrangement, the radiant ray was irradiated separately from the right and left-side positions, as in photography of the acryl box, under the condition of 3 mAs X-ray dosage, an image was recorded in two IPs, respectively and these two images were read. Since the distribution of X-ray dosage on the IP surface differs between irradiation of the X-ray from the left side and that from the right side, the dosage was compensated for such difference. If two X-ray bulbs are used, the distribution of the X-ray dosage can be adjusted to be approximately equal and therefore this compensation is not required.

From comparison of two images and checking of the image positions of lead pellets, it is known that the images are observed over three lines with the same number and a distance between these images, that is, the maximum distance Δmax is approximately 6.7 mm and 52 rows (number of pixels). The distance from the IP surface to the photographing part housing is 20 mm and the distance from the IP surface to the X-ray bulb is 2020 mm as in the case of the acryl case and therefore the minimum distance Δmax which permits the presence of pixels to be paired is 0.4 mm and five rows (number of pixels). Accordingly, under this photographic condition, an inter-row distance which permits a pair of pixels is within the range of five rows or over and 52 rows or less.

The pixel values of pixels of all corresponding lines and rows of two images were divided by 2 and resultant values were added to each other, that is, two images were averaged to obtain one image. Consequently, the image obtained is equivalent to an image obtained by simultaneously irradiating the radiant ray from two X-ray bulbs whose angles were set to be different. The phantom which does not move, differing from a live human body, permits to obtain an image corresponding to the one-image system by synthesizing the images obtained by the two-image system. In the case of the accelerated phosphorescence fluorescent object, a fading phenomenon occurs that the quantity of light emission of the accelerated phosphor varies with the lapse of time from irradiation of the radiant ray to reading of the image and therefore direct photography of one image on one IP by the time-delayed 2-shot photography is not preferable because the pixel vales of a pair of pixels have differ from one another.

Figure 13:
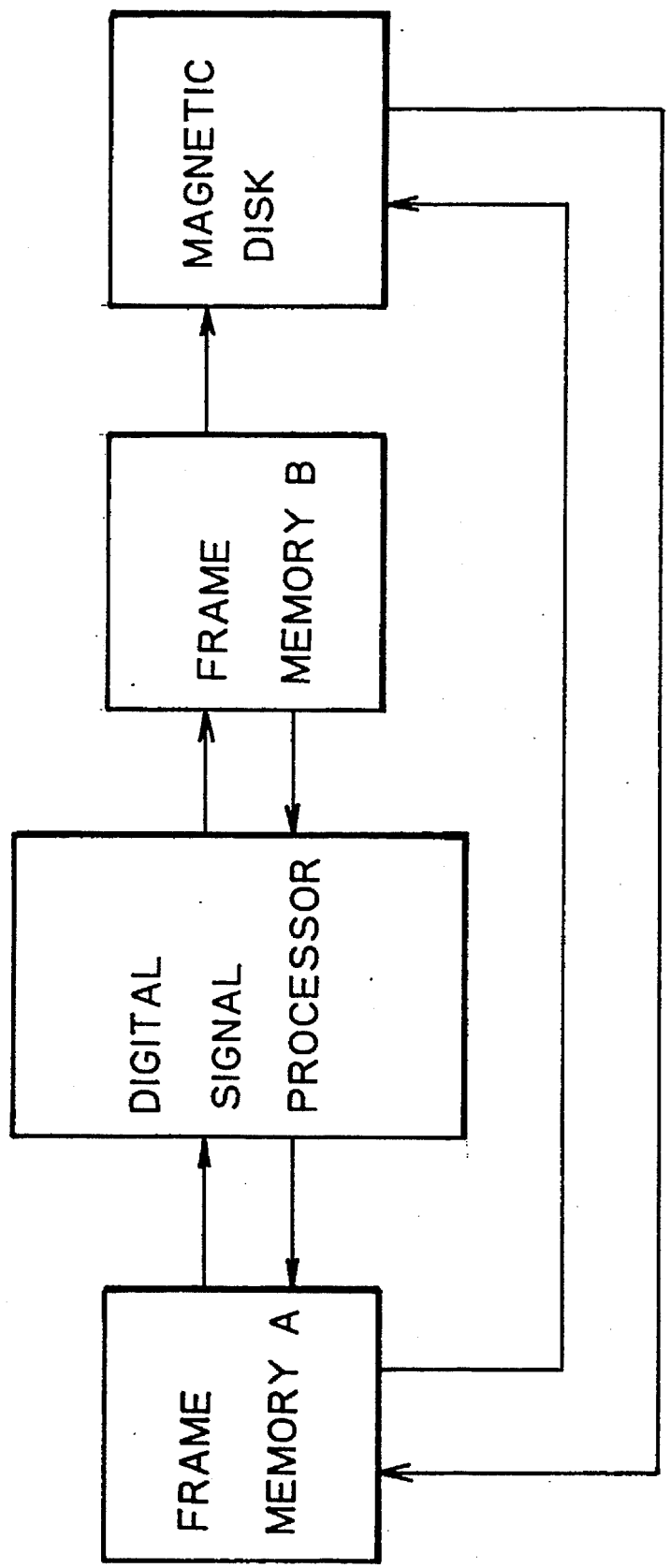
FIG. 13 is an illustration showing a configuration example of an image processing unit.

Description of Method for Standardization of Pixel Values 3-dimensional images were processed by using a work station (SUN4/370), two frame memories A and B and a digital signal processor (DSP, Super Card made by CSPI, USA), and the images after processing were stored in a magnetic disk. The configuration is shown in FIG. 13.

Figure 14:
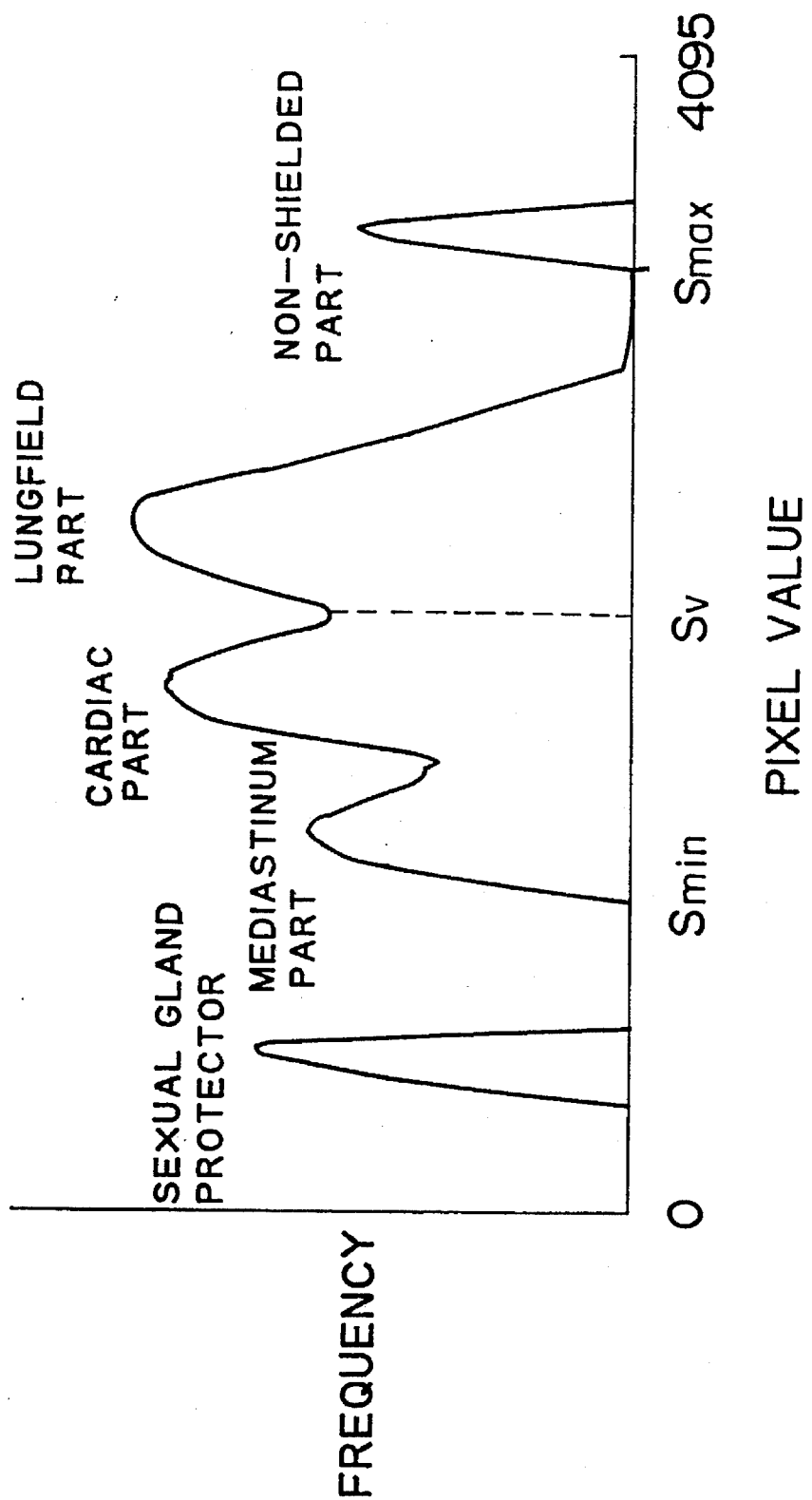
FIG. 14 is an example of a histogram.
Figure 15A:
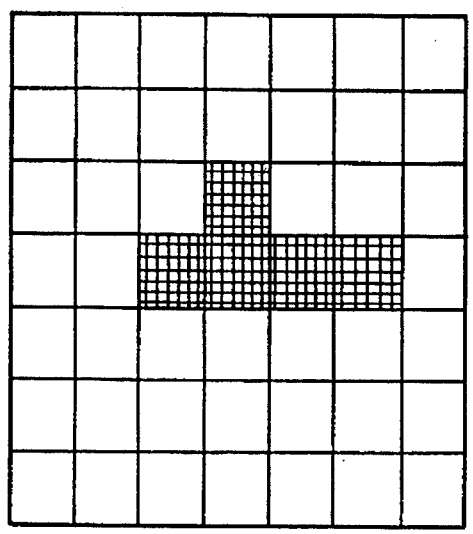
Figure 15B:
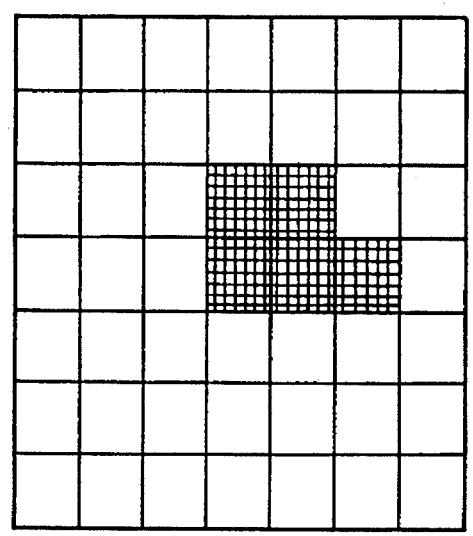
Figure 15C:
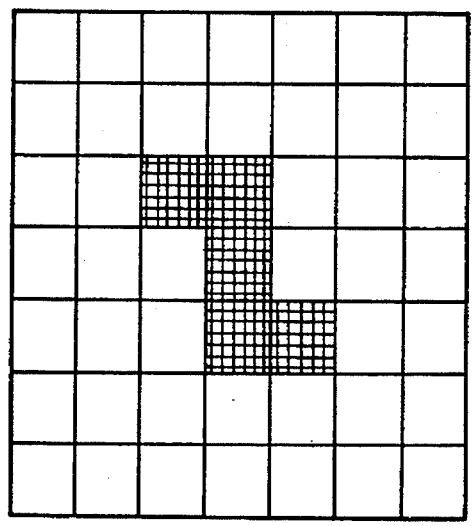
Figure 15D:
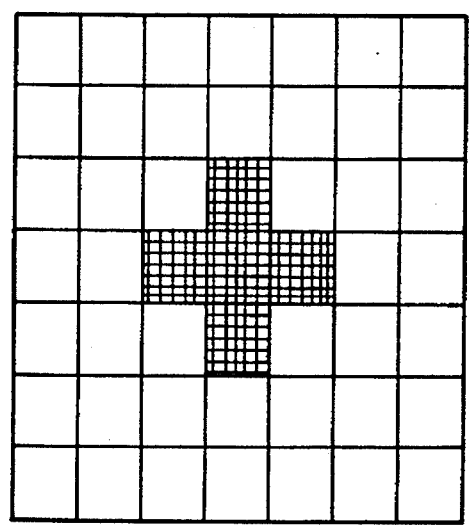

One image of 4096 rows×4974 lines obtained as described above was decimated to an image of 512 rows× 622 lines and a histogram of pixel values as shown in FIG. 14 was prepared. In the histogram shown in FIG. 14, a peak where the pixel value is least pertains to an area of the sexual gland protector. A peak where the pixel value is largest pertains to an area of direct irradiation. Of three peaks at the intermediate part, a peak with a large pixel value (a right side part) pertains to the lung field, a peak with a small peak value (a left side part) pertains to the mediastinal part and the diaphragmatic part, and a peak at the center pertains to the cardiac part. In other words, the image information of a human body is obtained only from the pixel values of the intermediate part with three peaks, and these pixel values of the intermediate part, that is, those pixel values of the par between Smin and Smax shown in FIG. 14 are standardized as 8-bit pixel values from 0 to 511. All pixel values of the pixels having the pixel values of Smin or under are regarded as 0 and al pixel values of Smax or over, as 511. In this case, the pixel values of the bottom between two peaks at the right side are regarded as Sv.

Description of the Smoothing Method

After an image stored in the magnetic disk has been transferred to the frame memory A (refer to FIG. 13), data of 4096 rows×32 lines are transferred from an image of 4096 rows×4974 lines are transferred to the memory in the DSP to form 7 rows×7 lines matrices in order and a mean value Sm is calculated. If Sv≧Sm is known as a result of comparison, Sm is substituted for the pixel value of the isolated pixel only when the processed pixels of the center are the completely isolated pixels with continuity 1 as compared with the pixel values of pixels of the ambiance. If Sv<Sm, Sm is substituted for Sv with respect to the pixels which are completely isolated with the continuity of five continuous pixels or less. However, even though the continuity is 5 or under, substitution does not apply if irradiation of the radiant ray reaches an end of the mask. In this case, the continuity with an adjacent pixel is evaluated depending on whether the difference between the processed pixel and the pixel value of the adjacent pixel is within ±2 and, when the difference is within ±2, it is recognized that there is a continuity between these pixels.

Next, a mask which is shifted by one row is prepared and similar processing of the adjacent pixel is carried out. When the isolativity and continuity of all rows of the fourth line are thus recognized as described above, processing of the next line is similarly carried out. Images of the 31st line to the 62nd line are transferred and similarly processed when the processing of up to the 30th line has been finished. Thus all images up to the 4974th line are smoothed. Though, in this processing, the range of three lines and three rows in the periphery of the image cannot be processed, it is only a range of 0.3 mm in actual measurement and therefore no substantial problem will arise.

There are several cases where the continuity is 5 as, for example, shown in FIG. 15. Whether the continuity of 5 or less should be used as a reference for smoothing or the continuity of a larger number of pixels, for example, the continuity of 9 to 15, should be used as the reference for smoothing depends on the S/N ratio of the image which is determined in accordance with X-ray radiation dosage. In this embodiment, the continuity of 5 or less is sufficient as the reference for smoothing.

Isolated shadows such as quantum noise were reduced by this smoothing, graininess of the image was greatly improved and complexity in the process of recognition of the continuity described later could be eliminated. This smoothing can be simultaneously carried out in the process for recognizing the continuity described below.

Description of Continuity Recognizing Method

In this embodiment, determination of pixels to be paired in one line of the original image and recognition of the continuity on a 2-dimensional plane over several lines of the original image were simultaneously carried out. Processing for recognizing the continuity in this embodiment was carried out from the end face of the left-side lung field, that is, the upper end of the IP in FIG. 5. In this case, an image of some pixels from the zeroth row is included in the region of the non-shielded part and therefore all pixel values are regarded as 511. Some pixels nearby the 4095th row are included in the region of the sexual gland protector and therefore all pixels are regarded as 0. Though processing can be carried out from either the right side or the left side of the image by reversing the image, the processing was carried out with the address of the image of the left-side lung as a smaller address number as described above in this embodiment. The range of rows where the image information of a human body except for the upper part of the shoulder to the neck exists covers 500 or 1500 rows to approximately 3800 rows.

An image of the zeroth row to the 4095th row of the zeroth line to the 31st line was transferred to the memory of the calculating part and the following calculation was executed. In this case, the image position and the pixel value of the original image is expressed as S (i, j), where S denotes the pixel value, i denotes the line number, j denotes the row number and a position at the upper left-side corner of the IP is denoted by i=0 and j=0. The 3-dimensional position and the components of the pixel value are expressed as (P, x, y, z), where x denotes a position in the horizontal direction of the subject, y denotes that in the vertical direction of the subject and z denotes that in the direction of thickness, and these x, y and z values respectively denote the number of pixels obtained by dividing the actual dimensions by the pixel dimensions and the origin shall be set at the position of i=0 and j=0 on the IP.

(1) Recognition of the continuity in the direction of row in one line

The following calculation is carried out for j=0 to j=4095.

$$\Delta S = |S(i, j) - S(i, j+1)| \quad (5)$$

If $\Delta S > 2$, it shall be recognized that there is no continuity is recognized and the processing advances to the next number j.

If $\Delta S \leq 2$, it shall be recognized that there is a continuity and the calculation according to equation (6) is carried out for "j" after the next number until the continuity is lost.

$$\Delta S = |S(i, j) - S(i, j+n)| \quad (6)$$

A group of continuous pixels were stored with the first pixel and the number of continuous pixels (final pixel) as {S (i, j), S (i, j+N)}.

It should be noted that there were rarely isolated pixels which are completely discontinuous even though only the row direction of the image after smoothing was checked.

(2) Recognition of the continuity over a plurality of lines

The variations of pixel values in the row direction in one line comprise, as shown in FIG. 16, a directly irradiated region where the pixel value is 509 to 511, a central region (a region of j=jst~jed) which includes the image information of a human body and a region of the sexual gland protector where the pixel value is 0 to 2. Since the directly irradiated region and the sexual gland protector region have already been discriminated, calculation is carried out with respect to the central area (the region of j=jst~jed) which includes the image information of a human body.

In the case of only one continuous structural object, simple discrete pixel values are continued as shown in FIG. 17. Accordingly, a pair of pixel groups could be identified by confirming that m is within the range of $\Delta$min and $\Delta$max, pixel values S (i, J) and S (i, J+m) are within the same difference, and n of S (i, J) and n of S (i, J+m) are within the same difference. Equation (5) was used for comparison of pixel values. 3-dimensional positions were obtained using equations (1) and (3) for the determined pair of pixel groups.

In this case, m was used as the distance XL–XR between right and left-side pixels.

However, in the case that there are three or more (four in FIG. 19) structural objects which show same S, m and n values in the range of Δmin and Δmax as shown in FIG. 18 and, in addition, in the case that there was a possibility that the pixels of these structural objects form each other a plural number of pairs, those pixels with such pairing "possibility" was stored.

FIG. 19 shows a plurality of structural objects which are overlapped and FIG. 20 shows a disassembled illustration of such overlapping structural objects. In FIG. 19 showing a plurality of overlapping continuous structural objects, a composite image may include parts (c and d) where the same pair can be found with respect to value n but a pair of objects cannot be found in other almost all parts. In such case, this region as a whole was stored as of "unknown" pairs.

In similar processing of the next line, the groups of continuous pixels which can be defined as pairs and the groups of pixels which can be identified by "possibility" and "unknown" were stored. When the stored data of these lines coincide with each other, as j is within j±2 and S is within S±2 with respect to the defined pairs, in collation with the stored data of the preceding line, it was determined that there is a continuity of pixels at 3-dimensional positions.

Figure 11:
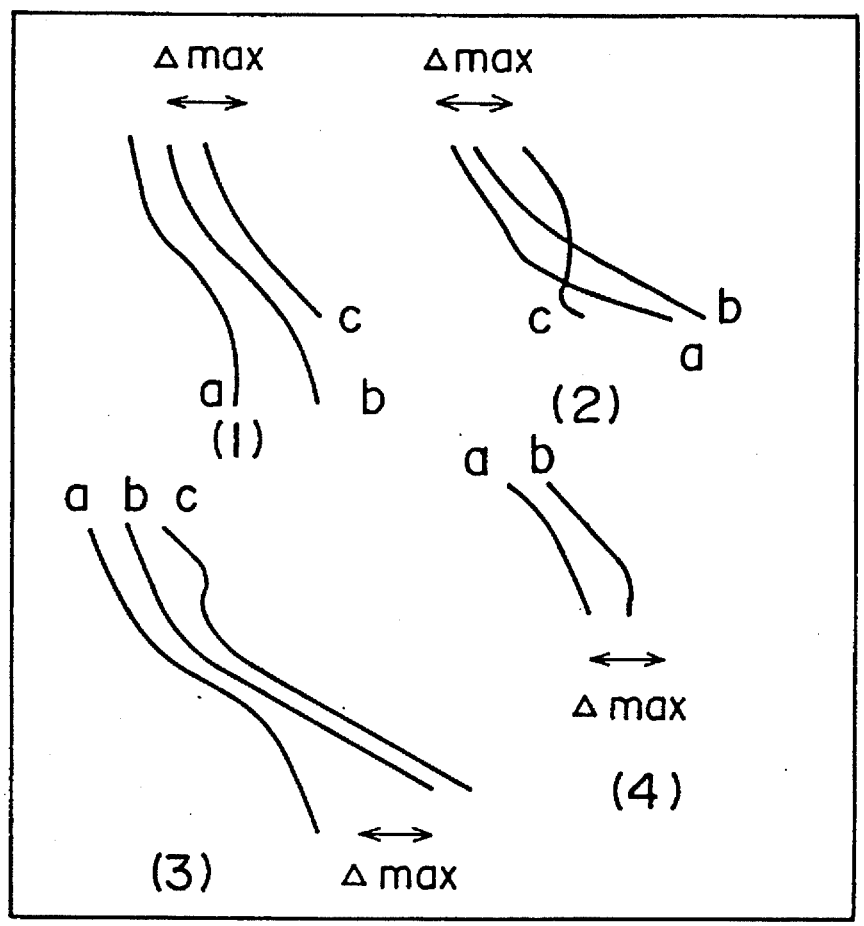
FIG. 11 is a typical diagram showing a continuity of pixels to be paired.
Figure 12:
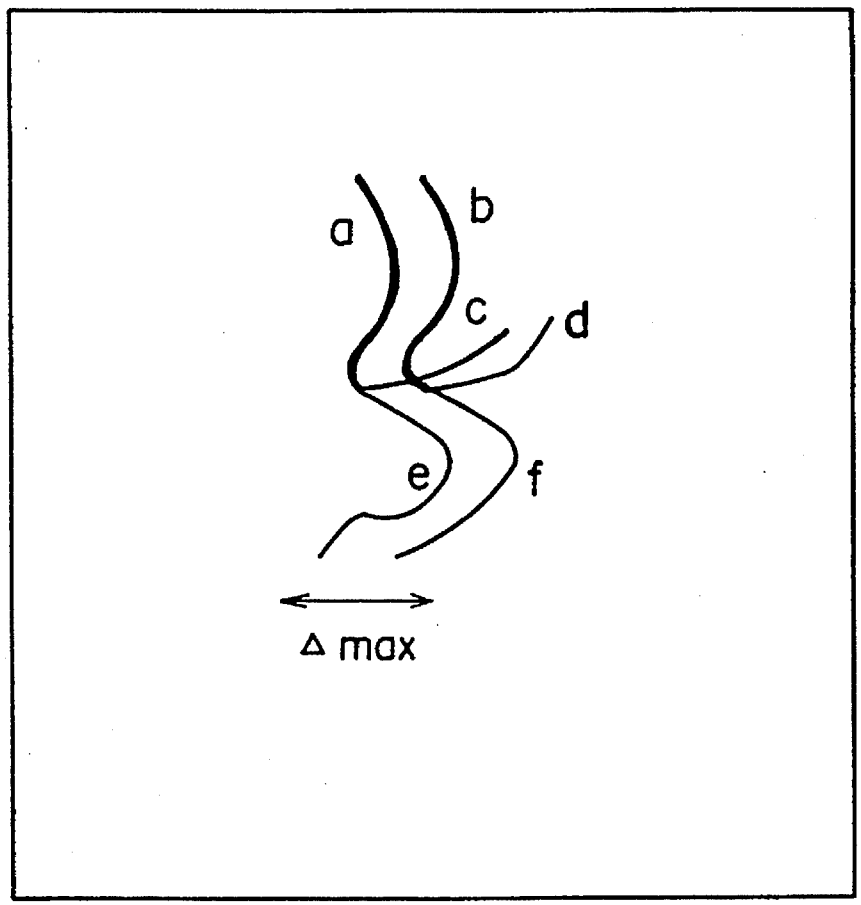
FIG. 12 is a typical diagram showing a continuity of pixels to be paired.

When the processing of several lines to several tens of lines has been finished, it was found that a group of simple discrete pixels exist in the vicinity of a group of "possibility" pixels and a group of "unknown" pixels. In other words, in the case of "possibility" pixels as shown in FIG. 18, the continuity of pixels which carry the possibility of pairing is discontinued (FIG. 11 (1) $c$), enters into the range of Δmin (FIG. 11 (2) $c$) or deviates from the range of Δmax (FIG. 11 (3) $a$), and consequently only a group of paired pixels will remain.

(3) Recognition of the group of paired pixels when a plurality of paired pixels are overlapped Back to the ambiance of the j row of the i−1 line which has been "unknown", the following pair of pixels $$[\{S(i-1, j\pm 2), S(i-1, j+n\pm 2)\},$$
$$\{S(i-1, j+m\pm 2), S(i-1, j+m+n\pm 2)\}]$$

which continue to the defined pair in the i line $$[\{S(i, j), S(i, j+n)\}, \{S(i, j+m), S(i, j+m+n)\}]$$

are determined as a pair of continuous pixel groups.

Similarly, a pair of continuous pixel groups are defined for the i-n line which include "unknown" pixels and a pair of other pixel groups which include "unknown" pixels are determined and defined.

Similarly, when the processing of pixel groups of overlapping structural objects has been finished with respect to several tens of lines to more than a hundred lines, a pair of simple discrete pixel groups appeared nearby j. In this case, however, the pixels with the same pixel values cannot be found even if the processing is returned to the i-n line. In other words, when the pixels with the same pixel value did not exist near J of the preceding line, the pixel value in the i line was assumed as S and the pixel value of the base near j of the i line as S*, ΔS=S−S* was subtracted from the pixel value string near the i−1 line. In other words, the pixel value string shown in FIG. 20($a$) was obtained by subtracting the pixel value string shown in FIG. 20($b$) from the pixel value string shown in FIG. 19.

When, on the contrary, a pair of simple discrete continuous pixel value groups exist in the i line and a group of pixel values of overlapping structural objects appear in the i+1 line, a pair of pixel value groups could be easily found by subtracting ΔS=S−S* of the i line from the pixel value string near j of the i+1 line.

The above described method for decomposing the group of pixels overlapped with two pairs of pixel groups into the pairs of pixel groups is to solve simultaneous equations with two unknowns. However, the processing is more complicated in the case that a number of pairs of pixel groups are overlapped, and the following describes the processing in this case.

When a simple discrete pair of continuous pixel value groups exists in the i line and overlapping image groups appear in the i+1 line, there are two overlapping pixel groups and the analysis is as described above. In addition, however, overlapping pixel groups may appear in the i+n line in the case that, for example, two ribs of the chest and the back are overlapped and further blood vessels of the lung fields are overlapped. In this case, a continuity of an affected portion can be recognized by subtracting a difference ΔS=S−S* between the base pixel value and the pixel values of a pair of pixels of the i line from the pixel value of the i+n line and, in addition, the overlap of three continuous pixel value groups can be decomposed and the pixel groups to be paired can be identified by evaluating a difference between ΔS of the i+n−1 line and the pixel value group of the i+n line.

When, on the contrary, a group of overlapping pixels due to overlapping of a rib and a collarbone exist in the i line and a blood vessel overlaps with these structural objects in the i=1 line, the pixel value of the blood vessel can be obtained by evaluating a difference between the pixel value of pixels corresponding to the blood vessel and the base pixel values which are the pixel values of the projection images of the surrounding collarbone and rib. Or the overlap of three continuous pixel value groups can be decomposed and identified by assuming the ambiance of the overlapping pixel groups of the i=1 line as unknown pixels and calculating a difference ΔS from the base pixel values after a pair of simple discrete pixels have appeared. In other words, a group of overlapping pixels can be decomposed into pixel value components by sequentially solving simultaneous equations with three unknowns.

Method for storing 3-dimensional images

The space resolution in the direction of depth (Z direction) of a 3-dimensional image thus obtained was approximately 2 mm. This resolution was determined by a size of one pixel of the original image and stored as 128 tomographic images in the magnetic disk. Those pixels with the same pixel value continue in most cases. Therefore, in the case that all pixels in a part of coordinates y+n~y+n+q have the pixel value p on the x+m line of a certain tomographic image, the image was compressed in a shape specified by the equation given below:

$$\{p, (x=m, y+n), (x+m, y+n+q)\}$$

and in the case that all pixels in a square region with coordinates (x+m, y+n)~(x+m+r, y+n+q) on a certain tomographic image have the same pixel value p. the image was compressed in a shape specified by the equation given below:

$$\{p, (x=m, y+n), (x+m+r, y+n+q)\}$$

Thus the image could be stored with data less than the original image. For example, 38 images corresponding to the outside of a human body could be stored with data per image, that is, the identification number (z number) of the tomographic image in the direction of depth z and {511, (0, 0), (4095, 4973)}.

Display of the tomographic image

Since the pixels are stored as a tomographic image in the magnetic disk, the image can be displayed only by transferring the image corresponding to the z number to the memory of the CRT. After the image is transferred to the frame memory and processed with respect to the space frequency, the image can be displayed on the CRT, transferred to the laser printer and copied on a silver halide film. Transfer to these display systems is common to the display of other images.

Display of stereoscopic images

Two right and left-side projection images as viewed from one eye were formed according to a known art by designating the positions of both eyes for stereoscopic vision and the origin of the image (the rearmost point passing through the center of an image information which need be viewed from the center between the positions of both eyes).

Display of the erasable image of image information

Stereoscopic images were formed and two right and left-side images were displayed on the CRT while keeping a stereoscopic vision, and a pixel value component which continues to a designated part was erased by designating a part to be erased with two cursors, then a projection image of the remaining pixel value component was formed on the display. Though this method is complicated and troublesome and need be improved, it can be implemented unless such troublesomeness is avoided.

Display of the pixel value component of the bone

As described above, stereoscopic images were formed and two right and left-side images were displayed on the CRT, then a bone was designated by two cursors while keeping a stereoscopic vision and the designated pixel value component was displayed. Since a pixel of one position does not ensure the accuracy, at least ten positions were designated, and a list of pixel value components at each specified position of more than ten positions, a mean value of these pixel value components, for example, a standard value of a healthy person, and a difference from the standard value were displayed.

An embodiment using a radiation image recorded on a silver halide film is described below. The present invention does not show an essential difference in the use of the accelerated phosphorescence fluorescent material and in the used of the silver halide film and therefore the following describes only the outline of an embodiment using the silver halide film explained below.

The flow of image processing is shown in FIG. 21. In step 101 in FIG. 21, 2-dimensional radiant rays produces 2-dimensional pixel data which shows an image when a 2-dimensional radiation image, which is obtained by simultaneously irradiating the radiant ray from, for example, two directions with the angle of irradiation to a subject changed, is read by the digitizer (see FIG. 1), and these 2-dimensional image data are stored. In step 102, a pixel value component (a value in proportion to an absorption quantity of the radiant ray or a quantity in proportion to the transmission quantity of radiation) of each boxel is obtained based on the 2-dimensional pixel data and, in step 103, the result is stored. A 3-dimensional image is converted to a display image. In other words, two images, which must be obtained by independently irradiating the radiant ray from two directions is obtained from the 3-dimensional image, a tomographic image as viewed from an optional angle is formed and a projection image of the subject which is partly excluded. A display image thus obtained is stored once (step 105) and subsequently the stored display image is displayed on the CRT (step 106). For viewing two stereoscopic images, these images can be stereoscopically viewed by observing two CRT images with a stereoscopic image viewer or liquid crystal glasses which vary synchronized with repeated displays of right and left-side images or observing two color display images with filter glasses, and the depth of images can be displayed by designating with two cursors a part whose 3-dimensional positions should be known. After the images have been observed on the CRT, the images can be sent as required to a film printer to obtain hard copies through printing and development.

In addition, after the 3-dimensional image has been obtained, one image or two right and left-side images are displayed on the CRT, the pixel value of a bone of the corresponding part is displayed by pointing the trabeculae of the collarbone and the rib with the cursor and an index of bone density can be obtained from this pixel value. Though the X-ray CT does not provide the resolution enough measure the density of the trabecula, a method of simple photography according to the present invention provides the resolution enough to sufficiently display the trabecula of particularly a side of the human body and is available for measurement of the bone density. For measurement of the bone density, there is available a method for designating ten positions on the CRT and evaluating the bone density with a mean value.

The following describes an embodiment of the one-image system for a process of decomposing the image data into the pixel value components in the direction of thickness of the subject which is carried out in generation of a 3-dimensional image.

(1) A lead plate with a window of 7 inches in width and 8.5 inches in length is set above the chest of a subject person who is lying on his back on a prone-position type photography stand while being kept slightly away from him, two radiation sources are arranged approximately 1 m away from the subject, a silver halide film cassette is set fin parallel to a line along which the digitizer will read later beneath the subject, the radiant rays from two radiation sources are simultaneously irradiated to this film cassette to obtain one thoracic image.

(2) An image (512 rows×512 lines×8 bits) is read from this film by using the digitizer and stored in the frame memory, the magnetic disk or the like.

(3) Stored pixel data is read out and the pixel values are standardized so that the minimum value of the pixel data is 0 and the maximum value is 511, and the image is divided into the regions such as the lung field and the cardiac part based on the histogram of pixel values.

(4) An image of 0–31 lines is entered into the memory of a calculator; however, the maximum distance $\Delta max=16$ pixels.

(5) A matrix of 32×32 pixels is prepared. It is determined whether all pixels are checked for pairing of pixels in the group of $\Delta max=16$ pixels. It is determined which pixels of the zeroth to 15th pixels are to be paired with 16th to 31th and, if not so, the pixel values of row 0–row 15 are changed to 0. Because sixteen rows 0–15 are included in an image region formed only by the radiant ray irradiated from the right-side radiation source since the radiant ray from the left-side radiation source for sixteen rows 0–15 i shielded by the lead plate. This is the same with sixteen rows 496 to 511. For those pixels which have a possibility of pairing but are unknown as being paired are stored, the "possibility" of pairing is stored while the pixels values are kept as are. For the pixels which are recognized as pairs, the 3-dimensional positions are calculated by using equations (1) to (3).

The minimum value or the maximum value of the pixel values of a pixel group of row 15 to row -16 is stored as the base pixel value for processed pixels. Whether the minimum value or the maximum value should be selected as the base pixel value depends on the region on the image. For example, the maximum value is selected for the lung field and the minimum value for the cardiac part, mediastinal part and abdominal part.

(6) When the processing of up to the 15th line is finished, subsequently the data of line 16–line 32, line 33–. . . are entered and similarly processed. A pixel which continues to the pixel, which has been recognized as a pair in a certain line, in a direction of line can be easily recognized. If pixels of "possibility" of a pair of pixels which show the continuity but cannot be recognized as a pair are away from one another as far as more than the maximum distance $\Delta max$, "possibility" which has been stored is erased. For those pixels which cannot be recognized as being paired despite that they are located within the maximum distance $\Delta max$, the "possibility" is stored. When the pairs of pixels which have maintained the continuity are simultaneously discontinued, they are regarded as the pairs, all pixels concerned are regarded as the pairs and stored, and the possibility of pairing with other pixels is erased.

(7) Subsequently, the operation is repeated up to row 511 and the data of 512 rows×512 rows×8 bits is prepared again with respect to the pixels which have not been recognized as pairs. These data are prepared by substituting the base pixel values for the pixels which have been recognized as pairs. After this, simultaneous equations with ten or less unknowns are solved with respect to the pixels which are within the maximum distance $\Delta max$ and have the pixel values other than the base pixel values and the paired pixels are determined.

(8) Finally, pixel values of the base pixels are compared and the pixels which largely deviate from the maximum value or the minimum value and have the continuity are recognized as a continuous object.

(9) The subject is divided into 128 tomographic planes in the direction of depth and these divided planes are stored respectively. In this case, a memory of approximately 32 mega bytes is required ad the pixel values are stored in the magnetic disk or the frame memory after having been reversely compressed since almost all pixel values are the base pixel values.

The following describes an embodiment of the two-image system.

(1) A lead plate with a window of 7 inches in width and 8.5 inches in length is set above the chest of a subject person who is lying on his back on a prone-position type photography stand while being kept slightly away from him, a silver halide film cassette is set in parallel to a line along which the digitizer will read later and two radiation sources are arranged approximately 1 m away from the subject, and a film changer capable of replacing the film cassette within one second is installed at the lower part of the photography stand. Radiation photography is synchronized with the electrocardiography, the radiant ray is irradiated from one radiation source in the expansion period of the heart, the photographed film is sent to the film storing part and, at the same time, a new film is sent to the photographing part and the radiant ray is irradiated to the subject from the other radiation source. Thus two thoracic images are obtained by developing these two radiation-exposed films are obtained.

(2) Two images (512 rows×512 rows×8 bits) are read from this film by using the digitizer and stored in the frame memory or the magnetic disk.

(3) Images of row 0 to row 31 are entered into the memory of the calculator from the left-side image (the image obtained by irradiating from the left-side radiation source) and the right-side image (in this case, the maximum distance $\Delta max=16$ pixels).

(4) Matrices of 32×32 are prepared respectively for the right and left-side images. In this case, the pixel values of pixels of row 0 to row 15 of the left-side image are regarded as 0 (though there are the pixel values affected by the scattering X-ray, they are also regarded as 0). Those pixels to be paired are searched by comparing row 0 to row 15 of the right-side image and row 16 to row 31 of the left-side image. In this case, if the pixels of row 0 of the right-side image are not paired with those of row 16 of the left-side image, the pixel values of row 0 of the right-side image are changed to 0. Subsequently, recognition of the pair of pixel values is carried out in sequence. Of the pixels which are unknown as to whether or not they are paired, the pixels which have the possibility of pairing are stored. The two-image system provides a far higher probability of finding paired pixels than the simultaneous one-image system since there are no overlapping lines due to the radiant rays from the right and left-side radiation sources.

First, pixels having the same pixel value in each line are found and stored as a pair by recognizing their continuity over a plurality of lines. 3-dimensional positions of the pixels which have been recognized as pairs are calculated by using equations (1)~(3). In the case that the pixel values which continue in lines and rows are the minimum value or the maximum value in the 32×32 matrices, they are stored as the base pixels.

(5) Next, data of the 16th line are entered and similarly processed. Those pixels having the pixel values which continue to the pixels which have been previously recognized as pairs can be easily recognized. In the case that a pair of pixels which have shown the continuity but could not be recognized as the pair are away as far as more than the maximum distance $\Delta max$, the "possibility" which has been stored is erased. Those pixels which are in the range of the maximum distance $\Delta max$ but cannot be recognized are stored as "possibility". When the pixels having the continuity are simultaneously discontinued, these pixels are regarded as pairs and all pixels concerned are recognized and stored as pairs, and the possibility of pairing of these pixels with other pixels is erased.

(6) Subsequently, calculation is repeated up to row 511 and the data of 512 rows×512 rows×8 bits is prepared again with respect to the pixels which have not been completely recognized as pairs. These data are prepared by substituting the base pixel values for the pixels which have been recognized as pairs. After this, simultaneous equations with seven or less unknowns are solved with respect to the pixels which are within the maximum distance $\Delta max$ and have the pixel values other than the base pixel values and the paired pixels are determined respectively (7) Finally, pixel values of the base pixels are compared and the pixels which largely deviate from the maximum value or the minimum value are recognized as a continuous object.

(8) The subject is divided into 128 tomographic planes in the direction of depth and these divided planes are stored respectively. In this case, a memory of approximately 32 mega bytes is required ad the pixel values are stored in the magnetic disk or the frame memory after having been reversely compressed since almost all pixel values are the base pixel values.

As described above, this embodiment enables to substantially reduce the operation time since simultaneous equations are solved only with respect to unknown pixels after obtaining an image of an image line in parallel to the epipolar line, applying a concept of recognition of the maximum distance Δmax, base pixel values, and continuity of the projection image and determining the 3-dimensional positions. Other calculating methods utilizing seven preconditions or assumptions, or due preconditions disclosed in the present invention can be considered and are duly involved in the present invention. In addition, analyses using fuzzy and neuro models are also available from the present invention.

After decomposing one image obtained by simultaneous or sequential irradiation from two radiation sources or two images obtained by two times of irradiation with an interval interposed into respective pixel values in the direction of depth of the structural objects in the subject, the images can be displayed as various 3-dimensional images by using the information, and two images, which must be obtained from an image obtained by the one-image system by independently irradiating the radiant rays from two directions, can be obtained by adding up the pixel value components in the direction of depth on the same straight line from the projection angles from the radiation sources and the positions of the radiation sensors. Otherwise, an expansion-free image, differing from general radiation images, can be easily obtained by adding up the pixel value components in the direction of depth at the same positions (x, y).

The display of a stereoscopic image of a patient who requires an operation clearly serves as supplementary means for examination of the method of operation prior to actual operation. Combination of these information with the X-ray CT or MRI information can be used as more accurate diagnostic information.

Though, in the above embodiments, the method for thoracic images has been described, the present invention is applicable to any part of the body without limiting the method to physical parts such as the head, abdomen and upper and lower extremities and also applicable to subjects other than human body.

What is claimed is:

1. A method for generating 3-dimensional radiation images comprising a step for obtaining at least one 2-dimensional radiation image of a subject carried by a radiant ray which has passed through a subject is obtained by irradiating a radiant ray from a plurality of positions, which differ from one another, toward said subject; a step for obtaining 2-dimensional pixel data which denotes pixel values at respective points on said 2-dimensional radiation image by repeatedly scanning an image in a main scanning direction which intersects a sub-scanning direction while sequentially moving in said specified sub-scanning direction on this 2-dimensional radiation image; and a step for obtaining 3-dimensional pixel data which denotes the pixel values corresponding to 3-dimensional points inside said subject based on the 2-dimensional pixel data, wherein said 2-dimensional radiation image is one 2-dimensional radiation image obtained by simultaneously irradiating a radiant ray toward said subject from a plurality of irradiating positions which differ from one another.

2. A method for generating 3-dimensional radiation images in accordance with claim 1, wherein the radiant ray is irradiated to said subject whose parts other than a part from which said 3-dimensional image data is desired are covered with a radiation shield.

3. A method for generating 3-dimensional radiation images in accordance with claim 1, wherein said plurality of irradiating positions are set so that a straight line which connect through said plurality of irradiating positions extends in a direction corresponding to one of said main scanning direction and said subnscanning direction on said 2-dimensional radiation image.

4. A method for generating 3-dimensional radiation images in accordance with claim 1, wherein the radiant ray is irradiated onto said subject to which markers are attached to recognize a plurality of images of said markers which are obtained on said 2-dimensional radiation image, and an angle formed by a straight line, which connects through said plurality of images, and one of said main scanning direction and said sub-scanning direction is obtained.

5. A method for generating 3-dimensional radiation images in accordance with claim 1, wherein a maximum distance Δmax between a plurality of points formed on said 2-dimensional radiation image by a radiant ray which has been irradiated from a plurality of irradiating positions and has passed through one point inside said subject, respective pluralities of points corresponding to each point inside said subject on said 2-dimensional radiation image are evaluated within said maximum distance Δmax, and said 3-dimensional pixel data is obtained based on respective 2-dimensional pixel data obtained from said respective pluralities of points.

6. A method for generating 3-dimensional radiation images in accordance with claim 5, wherein the radiant ray is irradiated to said subject to which markers are attached at a radiation irradiation side thereof, a plurality of images of said markers obtained on said 2-dimensional radiation image are recognized, and said maximum distance Δmax is set according to distances among said plurality of images.

7. A method for generating 3-dimensional radiation images in accordance with claim 5, a plurality of points having the same pixel value which exist within said maximum distance Δmax with a specified permissible difference are regarded as a plurality of candidate points corresponding to the specified points in said subject, and said plurality of points corresponding to said specified points are found by recognizing a continuity of these candidate points on said 2-dimensional radiation image.

8. A method for generating 3-dimensional radiation images in accordance with claim 7, a representative pixel value of a plurality of pixels which exist within specified regions around respective pixels on said 2-dimensional radiation image is regarded as a base pixel value for said respective pixels and said continuity is recognized based on a differential component between the pixel values of respective pixels and said base pixel value.

9. A method for generating 3-dimensional radiation images in accordance with claim 5, a smoothing processing is given to said 2-dimensional radiation image based on said 2-dimensional pixel data for obtaining pluralities of points corresponding to respective points in said subject on said 2-dimensional radiation image.

10. A method for generating 3-dimensional radiation images in accordance with claim 9, wherein said smoothing processing differs with each region on said 2-dimensional radiation image.

11. A method for generating 3-dimensional radiation images in accordance with claim 1, wherein a desired tomographic image of said subject is generated according to said 3-dimensional image data and displayed.

12. A method for generating 3-dimensional radiation images in accordance with claim 1, wherein an image of said subject projected in a desired direction is generated according to said 3-dimensional pixel data and displayed.

13. A method for generating 3-dimensional radiation images in accordance with claim 1, wherein, in a case that said subject is an alive subject whose bone is partly cut away, an image of said subject projected in a desired direction is generated according to said 3-dimensional pixel data and displayed.

14. A method for generating 3-dimensional radiation images in accordance with claim 1, wherein, in a case that said subject is an alive subject, a pixel value of a bone of said subject is obtained according to said 3-dimensional pixel data and displayed.

15. A method for generating 3-dimensional radiation images in accordance with claim 1, wherein a plurality of 2-dimensional images which are projected in directions differing from one another as much as an angle corresponding to a parallax are generated and displayed.

16. A method for generating 3-dimensional radiation images in accordance with claim 1, wherein one of a silver halide film and an accelerated phosphorescence fluorescent is used as a radiation sensor for obtaining said 2-dimensional radiation image.

17. A method for generating 3-dimensional radiation images comprising a step for obtaining at least one 2-dimensional radiation image of a subject carried by a radiant ray which has passed through a subject is obtained by irradiating a radiant ray from a plurality of positions, which differ from one another, toward said subject; a step for obtaining 2-dimensional pixel data which denotes pixel values at respective points on said 2-dimensional radiation image by repeatedly scanning an image in a main scanning direction which intersects a sub-scanning direction while sequentially moving in said specified sub-scanning direction on this 2-dimensional radiation image; and a step for obtaining 3-dimensional pixel data which denotes the pixel values corresponding to 3-dimensional points inside said subject based on the 2-dimensional pixel data, wherein said 2-dimensional radiation image is one 2-dimensional radiation image obtained by sequentially irradiating a radiant ray toward said subject from a plurality of irradiating positions which differ from one another.

18. A method for generating 3-dimensional radiation images in accordance with claim 17, wherein the radiant ray is irradiated to said subject whose parts other than a part from which said 3-dimensional image data is desired are covered with a radiation shield.

19. A method for generating 3-dimensional radiation images in accordance with claim 17, wherein said plurality of irradiating positions are set so that a straight line which connect through said plurality of irradiating positions extends in a direction corresponding to one of said main scanning direction and sub-scanning direction on said 2-dimensional radiation image.

20. A method for generating 3-dimensional radiation images in accordance with claim 17, wherein the radiant ray is irradiated onto said subject to which markers are attached to recognize a plurality of images of said markers which are obtained on said 2-dimensional radiation image, and an angle formed by a straight line, which connects through said plurality of images, and one of said main scanning direction and said sub-scanning direction is obtained.

21. A method for generating 3-dimensional radiation images in accordance with claim 17, wherein a maximum distance Δ max between a plurality of points formed on said 2-dimensional radiation image by a radiant ray which has been irradiated from a plurality of irradiating positions and has passed through one point inside said subject, respective pluralities of points corresponding to each point inside said subject on said 2-dimensional radiation image are evaluated within said maximum distance Δmax, and said 3-dimensional pixel data is obtained based on respective 2-dimensional pixel data obtained from said respective pluralities of points.

22. A method for generating 3-dimensional radiation images in accordance with claim 21, wherein the radiant ray is irradiated to said subject to which markers are attached at a radiation irradiation side thereof, a plurality of images of said markers obtained on said 2-dimensional radiation image are recognized, and said maximum distance Δmax is set according to distances among said plurality of images.

23. A method for generating 3-dimensional radiation images in accordance with claim 21, a plurality of points having the same pixel value which exist within said maximum distance Δ max with a specified permissible difference are regarded as a plurality of candidate points corresponding to the specified points in said subject, and said plurality of points corresponding to said specified points are found by recognizing a continuity of these candidate points on said 2-dimensional radiation image.

24. A method for generating 3-dimensional radiation images in accordance with claim 23, a representative pixel value of a plurality of pixels which exist within specified regions around respective pixels on said 2-dimensional radiation image is regarded as a base pixel value for said respective pixels and said continuity is recognized based on a differential component between the pixel values of respective pixels and said base pixel value.

25. A method for generating 3-dimensional radiation images in accordance with claim 21, a smoothing processing is given to said 2-dimensional radiation image based on said 2-dimensional pixel data for obtaining pluralities of points corresponding to respective points in said subject on said 2-dimensional radiation image.

26. A method for generating 3-dimensional radiation images in accordance with claim 25, wherein said smoothing processing differs with each region on said 2-dimensional radiation image.

27. A method for generating 3-dimensional radiation images in accordance with claim 17, wherein a desired tomographic image of said subject is generated according to said 3-dimensional image data and displayed.

28. A method for generating 3-dimensional radiation images in accordance with claim 17, wherein an image of said subject projected in a desired direction is generated according to said 3-dimensional pixel data and displayed.

29. A method for generating 3-dimensional radiation images in accordance with claim 17, wherein, in a case that said subject is an alive subject whose bone is partly cut away, an image of said subject projected in a desired direction is generated according to said 3-dimensional pixel data and displayed.

30. A method for generating 3-dimensional radiation images in accordance with claim 17, wherein, in a case that said subject is an alive subject, a pixel value of a bone of said subject is obtained according to said 3-dimensional pixel data and displayed.

31. A method for generating 3-dimensional radiation images in accordance with claim 17, wherein a plurality of 2-dimensional images which are projected in directions differing from one another as much as an angle corresponding to a parallax are generated and displayed.

32. (NEW) A method for generating 3-dimensional radiation images in accordance with claim 17, wherein one of a silver halide film and an accelerated phosphorescence fluorescent is used as a radiation sensor for obtaining said 2-dimensional radiation image.

* * * * *

UNITED STATES PATENT AND TRADEMARK OFFICE
CERTIFICATE OF CORRECTION

PATENT NO. : 5,623,528
DATED : April 22, 1997
INVENTOR(S) : Shiro TAKEDA

It is certified that error appears in the above-indentified patent and that said Letters Patent is hereby corrected as shown below:

TITLE PAGE [56] OTHER REFERENCES CITED

Insert --"EXTRACT TRANSLATION OF 'NANZANDO'S MEDICAL DICTIONARY'" pg. 1338-1339--.

Column 8

Line 44, "mirradiated" should be --irradiated--.

Column 22

Line 40, "fin" should be --in--.

Signed and Sealed this

Twenty-second Day of July, 1997

Attest:

BRUCE LEHMAN

Attesting Officer

Commissioner of Patents and Trademarks